(12) United States Patent
Morales Sánchez et al.

(10) Patent No.: US 11,365,208 B2
(45) Date of Patent: Jun. 21, 2022

(54) SILYLATED DERIVATIVES OF RESVERATROL AND THE USE THEREOF IN NEURODEGENERATIVE, NEUROLOGICAL OR INFLAMMATORY DISEASES

(71) Applicant: Consejo Superior De Investigaciones Cientificas, Madrid (ES)

(72) Inventors: Juan Carlos Morales Sánchez, Granada (ES); Pablo Peñalver Puente, Granada (ES); Efres Belmonte Reche, Granada (ES); Elena González Rey, Granada (ES); Maria Luisa Mateos Martin, Granada (ES)

(73) Assignee: Consejo Superior De Investigaciones Cientificas, Madrid (ES)

( * ) Notice: Subject to any disclaimer, the term of this patent is extended or adjusted under 35 U.S.C. 154(b) by 0 days.

(21) Appl. No.: 16/465,536

(22) PCT Filed: Nov. 23, 2017

(86) PCT No.: PCT/ES2017/070776
§ 371 (c)(1),
(2) Date: May 30, 2019

(87) PCT Pub. No.: WO2018/100219
PCT Pub. Date: Jun. 7, 2018

(65) Prior Publication Data
US 2019/0284213 A1    Sep. 19, 2019

(30) Foreign Application Priority Data

Nov. 30, 2016 (ES) ................ P 201631535

(51) Int. Cl.
| | | |
|---|---|---|
| *C07F 7/18* | (2006.01) | |
| *C07H 7/04* | (2006.01) | |
| *C07C 39/21* | (2006.01) | |
| *A61K 31/695* | (2006.01) | |
| *C07F 7/08* | (2006.01) | |
| *A61P 25/28* | (2006.01) | |
| *A61P 29/00* | (2006.01) | |

(52) U.S. Cl.
CPC .......... *C07F 7/1804* (2013.01); *A61K 31/695* (2013.01); *A61P 25/28* (2018.01); *A61P 29/00* (2018.01); *C07C 39/21* (2013.01); *C07F 7/08* (2013.01); *C07H 7/04* (2013.01)

(58) Field of Classification Search
CPC ............ C07F 7/1804; C07F 7/08; C07H 7/04; C07C 39/21; C07C 39/215
See application file for complete search history.

(56) References Cited

U.S. PATENT DOCUMENTS 6,552,213 B1 * 4/2003 Deshpande ........... C07F 7/1892
556/440

FOREIGN PATENT DOCUMENTS

| CN | 102675100 A | 9/2012 |
|---|---|---|
| CN | 103709050 A | 4/2014 |
| CN | 103922981 B | 1/2017 |
| JP | 2015-164903 A | 9/2015 |
| KR | 10-2012-0056586 A | 6/2012 |
| WO | WO 2003/086414 A1 | 10/2003 |
| WO | WO 2011/073482 A1 | 6/2011 |
| WO | WO 2015/162265 A1 | 10/2015 |

OTHER PUBLICATIONS

Azzolini, M. et al "Synthesis and evaluation of prodrugs . . . " Mol. Pharmaceutics, vol. 12, pp. 3441-3454. (Year: 2015).*
Lu, C. et al "Design, synthesis, and evaluation of resveratrol derivatives . . . " Bioorg. Med. Chem., vol. 22, pp. 7683-7687. (Year: 2012).*
Pezzuto, J. "Resveratrol: twenty years of growth, development and controversy" Biomol. Ther., vol. 27, No. 1, pp. 1-14. (Year: 2019).*
Kjaer, T. et al "No beneficial effects of resveratrol on the metabolic syndrome . . . " J. Clin. Endocrinol. Metab., vol. 102, No. 5, pp. 1642-1651. (Year: 2017).*
Li, C. et al "Resveratrol derivatives . . . " Exp. Opin. Ther. Patents, vol. 26, No. 10, pp. 1189-1200. (Year: 2016).*
Biasutto, L. et al "Resveratrol derivatives as a pharmacological tool" Ann. NY Acad. Sci., vol. 1403, pp. 27-37. (Year: 2017).*
Pouladi, M. et al "Choosing an animal model for the study of Huntington's disease" Nature Rev., vol. 14, pp. 708-721. (Year: 2013).*
Azorin-Ortuño et al., "Effects of long-term consumption of low doses of resveratrol on diet-induced mild hypercholesterolemia in pigs: a transcriptomic approach to disease prevention," Journal of Nutritional Biochemistry 23 (2012) 829-837.
Byung Ho Park et al., "Total Synthesis of Chiricanine A, Arahypin-1, trans-Arachidin-2, trans-Arachidin-3, and Arahypin-5 from Peanut Seeds," J. Nat. Prod. 2011, 74, 644-649.
Crauste et al., "Synthesis and Evaluation of Polyunsaturated Fatty Acid-Phenol Conjugates as Anti-Carbonyl-Stress Lipophenols," Eur. J. Org. Chem. 2014, 4548-4561.
Dong-Liang Lu et al., "Influence of Glucuronidation and Reduction Modifications of Resveratrol on its Biological Activities," ChemBioChem 2013, 14, 1094-1104.
Hanamura et al., "Synthesis of acacetin and resveratrol 3,5-di-O-γ-glucopyranosideusing lipase-catalyzed regioselective deacetylation of polyphenolglycoside peracetates as the key step," Journal of Molecular Catalysis B: Enzymatic 128 (2016) 19-26.

(Continued)

*Primary Examiner* — Leigh C Maier

(74) *Attorney, Agent, or Firm* — Knobbe Martens Olson & Bear, LLP

(57) ABSTRACT

The present invention relates to a group of compounds derived from resveratrol having as substituents at least one silyl group which, in turn, can be substituted by different groups. The invention also relates to the therapeutic use of these compounds in inflammatory, neurological, and neurodegenerative diseases.

4 Claims, 13 Drawing Sheets

(56) References Cited

OTHER PUBLICATIONS

Hoshino et al., "Selective Synthesis and Biological Evaluation of Sulfate-Conjugated Resveratrol Metabolites," *J. Med. Chem.* 2010, 53, 5033-5043.

International Search Report received in PCT Application No. PCT/ES2017/070776, dated Mar. 6, 2018.

Kenealey et al., "Resveratrol Metabolites Do Not Elicit Early Pro-apoptotic Mechanisms in Neuroblastoma Cells," J. Agric. Food Chem. 2011, 59, 4979-4986.

Larrosa et al., "Preventive Oral Treatment with Resveratrol Pro-prodrugs Drastically Reduce Colon Inflammation in Rodents," J. Med. Chem. 2010, 53, 7365-7376.

Lucas et al., "A concise synthesis of glucuronide metabolites of urolithin-B, resveratrol, and hydroxytyrosol," Carbohydrate Research 344 (2009) 1340-1346.

Takaya et al. "Biomimic transformation of resveratrol,"Tetrahedron 61, 2005, vol. 61, p. 10285-10290.

Wang et al., "Resveratrol Glucuronides as the Metabolites of Resveratrol in Humans: Characterization, Synthesis, and Anti-HIV Activity," J Pharm Sci. Oct. 2004; 93 (10):2448-57.

Xu et al. "Design, synthesis and evaluation of a series of non-steroidal anti-inflammatory drug conjugates as novel neuroinflammatory inhibitors," International Immunopharmacology, 2015, vol. 25, pp. 528-537.

Zhang et al., "Synthesis of Mono- and Di-O-γ-D-glucopyranoside Conjugates of (E)-Resveratrol", Synthesis, No. 8, Apr. 19, 2006, pp. 1301-1306.

Chiu et al., "Synthesis, Hydrolytic Reactivity, and Anticancer Evaluation of N- and O-Triorganosilylated Compounds as New Types of Potential Prodrugs", 1982. J Pharm Sci, 71(5): 542-551.

Chu et al., "Particle Replication in Nonwetting Templates Nanoparticles with Tumor Selective Alkyl Silyl Ether Docetaxel Prodrug Reduces Toxicity", 2014. Nano Lett, 14(3):1472-6.

Falomir et al., "Cytotoxic, Antiangiogenic and Antitelomerase Activity of Glucosyl- and Acyl- Resveratrol Prodrugs and Resveratrol Sulfate Metabolites", 2016. Chem Bio Chem, 17(14): 1343-1348.

Ma et al., "Resveratrol as a Therapeutic Agent for Alzheimer's Disease", 2014. Biomed Research International, article ID 350516, 13 pages.

Mazzotti et al., "The assay of pterostilbene in spiked matrices by liquid chromatography tandem mass spectrometry and isotope dilution method", 2010. J Mass Spectrometry, 45(4): 358-363.

Millership and Shanks. "Prodrugs Utilizing Organosilyl Derivation: An Investigation of the Long-Term Androgenic and Myotrophic Activities of Silyl Derivatives of Testosterone", 1989. J Pharm Sci, 77(2):116-119.

Parrott et al., "Incorporation and Controlled Release of Silyl Ether Prodrugs from PRINT Nanoparticles", 2012. J Am Chem Soc, 134(18):7978-7982.

Office Action issued in CN Application No. 2017800737486, dated Oct. 29, 2021.

Office Action issued in JP Application No. 2019-528888, dated Aug. 12, 2021.

* cited by examiner

SILYLATED DERIVATIVES OF RESVERATROL AND THE USE THEREOF IN NEURODEGENERATIVE, NEUROLOGICAL OR INFLAMMATORY DISEASES

CROSS REFERENCE TO RELATED APPLICATIONS

This application is the U.S. National Phase under 35 U.S.C. § 371 of International Application No. PCT/ES2017/070776 filed Nov. 23, 2017, designating the U.S. and published as WO 2018/100219 on Jun. 7, 2018, which claims the benefit of Spanish Application No. P 201631535, filed Nov. 30, 2016.

The present invention relates to a group of compounds derived from resveratrol having as substituents at least one silyl group which, in turn, can be substituted by different groups. The invention also relates to the therapeutic use of these compounds in inflammatory, neurological, and neurodegenerative diseases. The present invention is thus encompassed within the field of pharmacochemistry and pharmacology.

BACKGROUND

Resveratrol is a phenolic compound. The chemical structure of the phenolic compounds consists of at least one aromatic ring and one hydroxyl group. And within the phenolic compounds, resveratrol is a stilbene, this group of phenolic compounds being characterized by a structure of two phenolic rings joined by two carbon atoms (C6-C2-C6). Resveratrol is present in grapes and products derived therefrom, such as wine, and in other foods, although in much smaller quantities, such as peanuts and some berries. In these foods, it is present in free form or as piceid (resveratrol-3-O-glycoside). This compound possesses antioxidant, anti-inflammatory, and antitumor properties that prolong the longevity of cells.

Resveratrol presents chemopreventive activity of cancer in trials that represented three main stages of carcinogenesis: it acts as an antioxidant and antimutagen, has anti-inflammatory effects and inhibits cyclooxygenase (COX) and hydroperoxidase, and induces cell differentiation in human promyelocytic leukemia. In addition, as indicated above, resveratrol has been extensively studied for its correlation with the cardiovascular utility of red wine. Neurological uses for resveratrol have also been proposed.

Considering the number of beneficial physiological effects that resveratrol presents, there have been numerous projects focused on obtaining derivatives of this molecule that improve their health-related properties. The document Int. Immunopharmacology 25 (2015) 528-537 explores the anti-inflammatory properties of various resveratrol derivatives and their potential as inhibitors of neuroinflammation.

J. Med. Chem 2010 Jul. 8; 53(13): 5033-5043 describes the synthesis of sulfated resveratrol derivatives and their effect on various physiological activities such as inhibition of TNF-α or the activity of cyclooxygenases.

The document WO2011/073482 describes resveratrol derivatives that contain glucidic substituents and that have the ability to modulate inflammation, especially in intestinal pathologies such as irritable bowel syndrome or Crohn's disease.

DESCRIPTION OF THE INVENTION

In a first aspect, the present invention relates to the use of a compound of the formula (I):

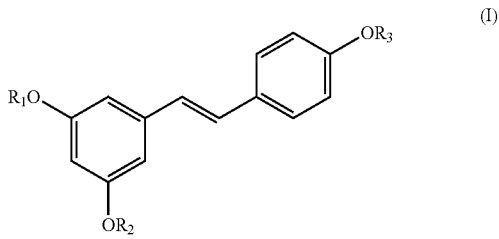

where $R_1$, $R_2$, and $R_3$ are selected independently from among an H, an $SiR_4R_5R_6$ group, an —NH(CO)$R_7$ group, or a carbohydrate,
where $R_4$, $R_5$, and $R_6$ are selected independently from among linear or branched $C_1$-$C_6$ alkyl or a phenyl group and $R_7$ is a linear or branched $C_1$-$C_{12}$ alkyl,
with the proviso that at least one of $R_1$, $R_2$, and $R_3$ is an $SiR_4R_5R_6$ group,
for the manufacture of a medicament for the treatment or prevention of inflammatory, neurological, or neurodegenerative diseases.

In a preferred embodiment, $R_1$ and $R_2$ are an $SiR_4R_5R_6$ group. In a more preferred embodiment, $R_3$ is H.

In another more preferred embodiment, $R_3$ is —NH(CO)$R_7$.

In another more preferred embodiment, $R_3$ is the following carbohydrate:

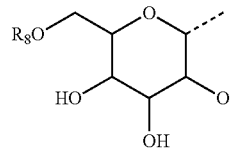

where $R_8$ is selected from among H or —C(O)—$R_9$, with $R_9$ being a $C_1$-$C_{22}$ alkyl group OR a $C_2$-$C_{22}$ alkenyl group.

In a more preferred embodiment, when $R_1$ and $R_2$ are an $SiR_4R_5R_6$ group, $R_4$ and $R_5$ are methyl, and $R_6$ is tert-butyl. In another more preferred embodiment, $R_4$, $R_5$, and $R_6$ are ethyl. In another more preferred embodiment, $R_4$, $R_5$, and $R_6$ are isopropyl.

In another preferred embodiment, $R_1$ and $R_3$ are an $SiR_4R_5R_6$ group.

In a more preferred embodiment, $R_2$ is H.

In another more preferred embodiment, $R_2$ is —NH(CO)$R_7$.

In another more preferred embodiment, $R_2$ is the following carbohydrate:

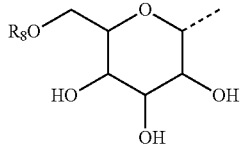

where $R_8$ is selected from among H or —C(O)—$R_9$, with $R_9$ being a $C_1$-$C_{22}$ alkyl group OR a $C_2$-$C_{22}$ alkenyl group.

In a more preferred embodiment, when $R_1$ and $R_3$ are an $SiR_4R_5R_6$ group, $R_4$ and $R_5$ are methyl, and $R_6$ is tert-butyl. In another more preferred embodiment, $R_4$, $R_5$, and $R_6$ are ethyl. In another more preferred embodiment, $R_4$, $R_5$, and $R_6$ are isopropyl.

In another more preferred embodiment, $R_1$, $R_2$ and $R_3$ are an $SiR_4R_5R_6$ group.

In a more preferred embodiment, when $R_1$, $R_2$, and $R_3$ are an $SiR_4R_5R_6$ group, $R_4$ and $R_5$ are methyl, and $R_6$ is tert-butyl. In another more preferred embodiment, $R_4$, $R_5$, and $R_6$ are ethyl. In another more preferred embodiment, $R_4$, $R_5$, and $R_6$ are isopropyl.

In another preferred embodiment, the compound of formula (I) is selected from the following group:

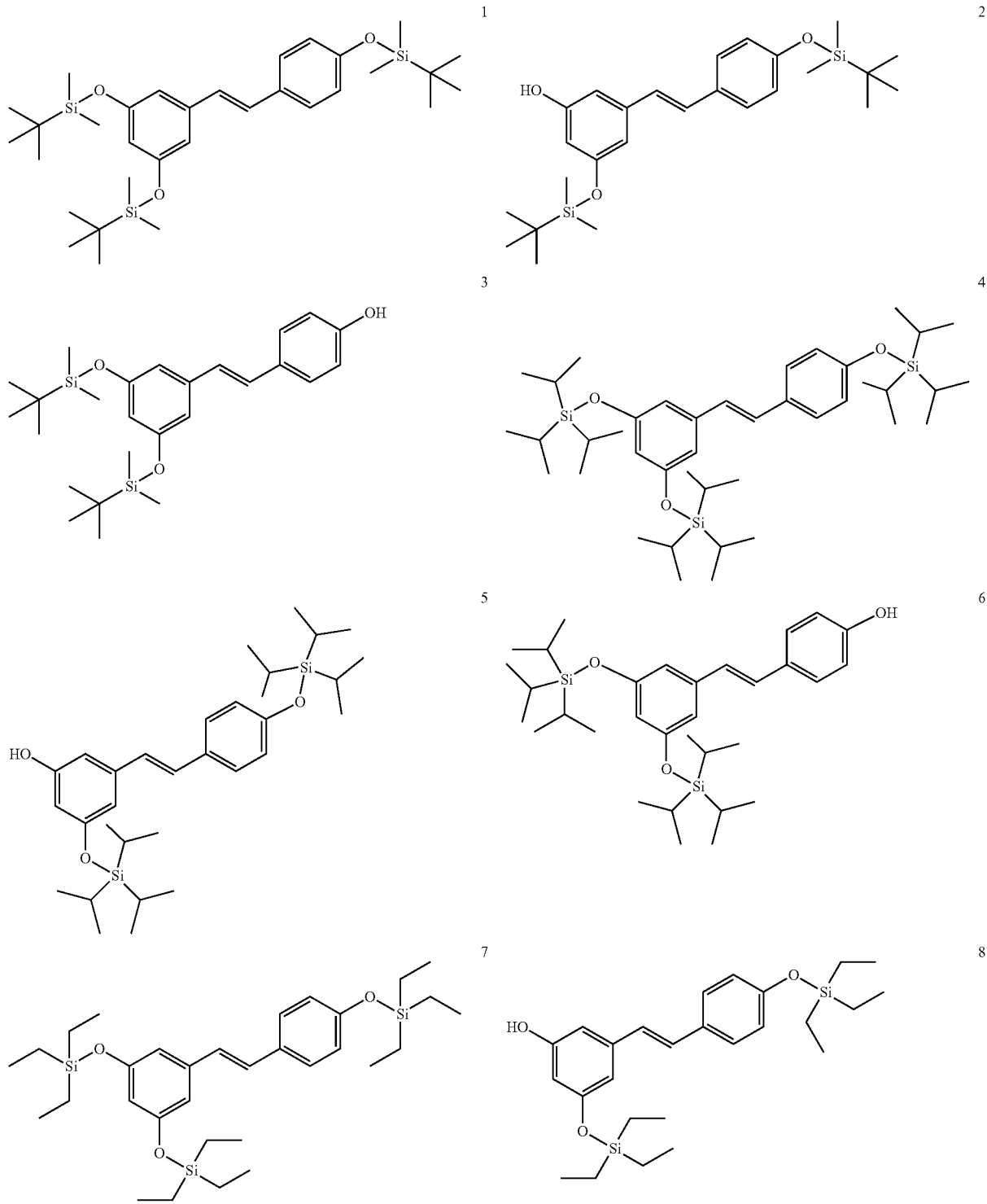

9
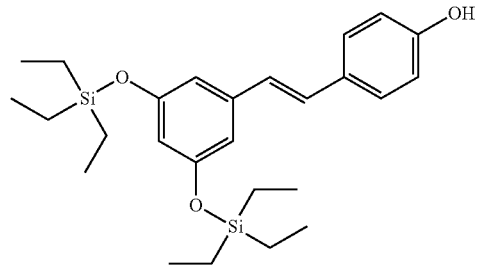
10
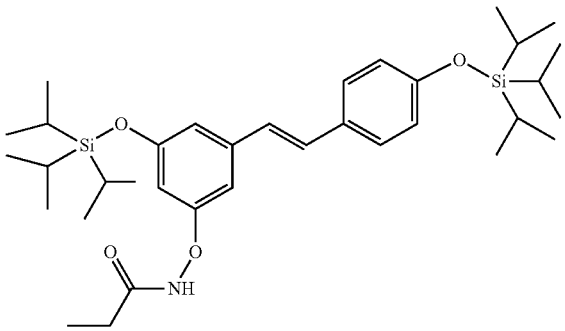
11
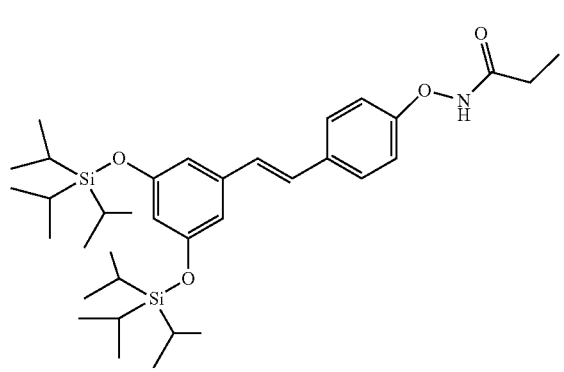
12
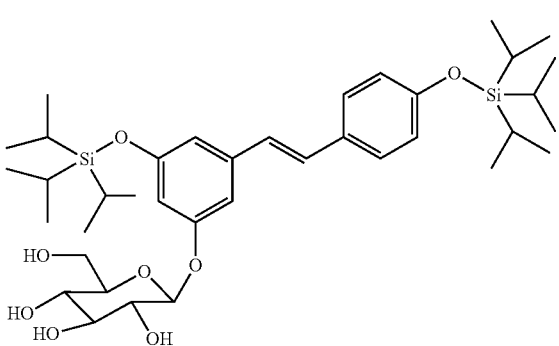
13
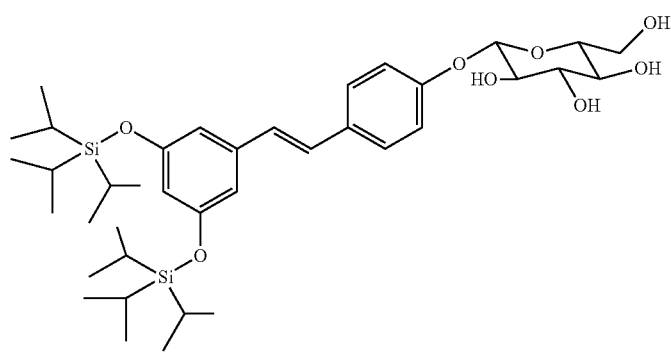
14
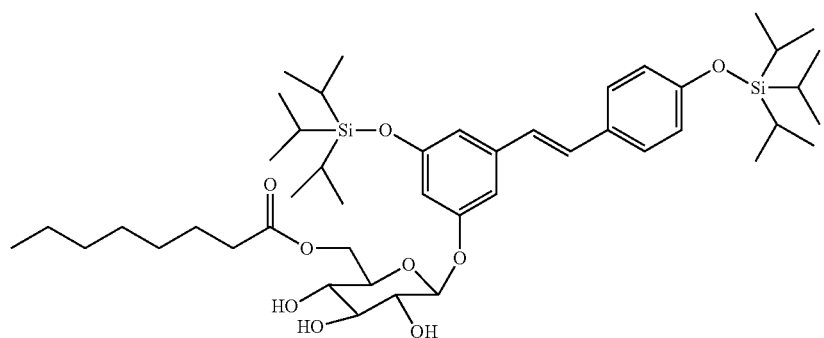

-continued
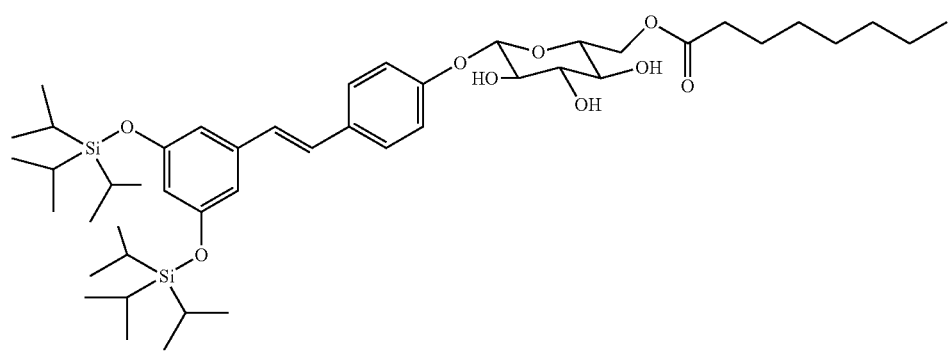
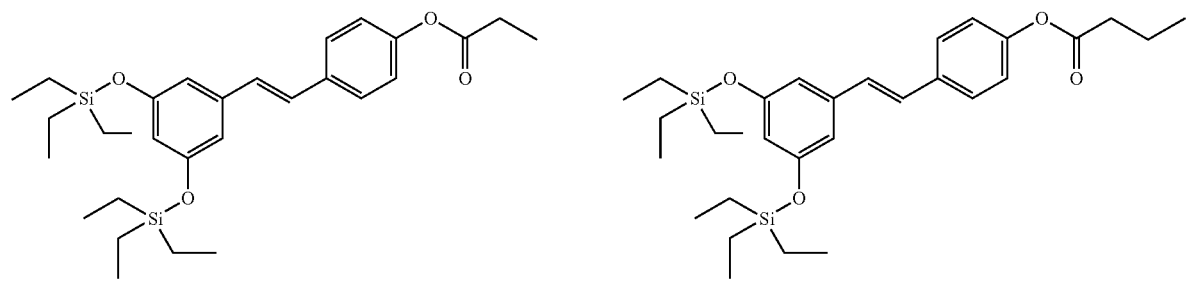
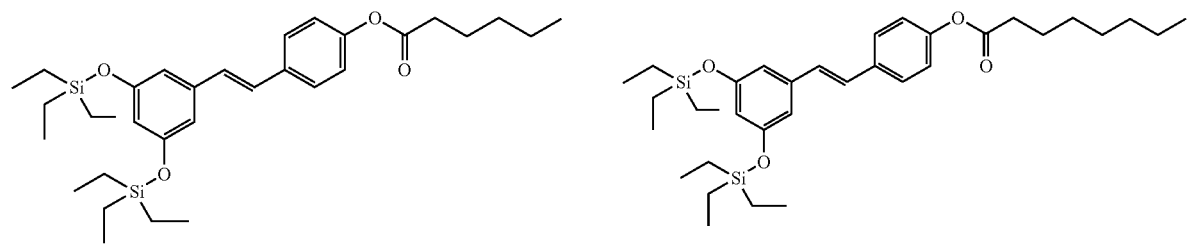

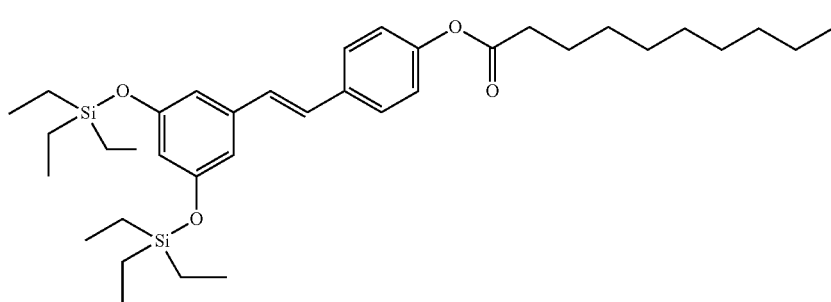

In a preferred embodiment, the neurological or neurodegenerative disease is selected from among Alzheimer's disease, Parkinson's disease, Huntington's disease, multiple sclerosis, amyotrophic lateral sclerosis, frontotemporal dementia, ischemia, and epilepsy.

Another aspect of the invention relates to a compound of formula (I'):

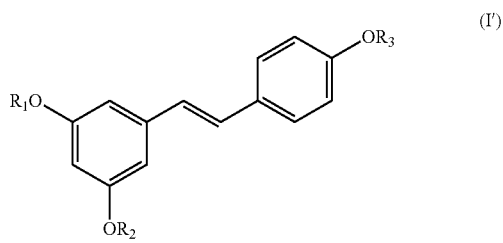

where $R_1$, $R_2$, and $R_3$ are selected independently from among an H, an $SiR_4R_5R_6$ group, an —NH(CO)$R_7$ group, or a carbohydrate, where $R_4$, $R_5$, and $R_6$ are selected independently from among linear or branched $C_1$-$C_6$ alkyl or a phenyl group and $R_7$ is a linear or branched $C_1$-$C_{12}$ alkyl, with the proviso that at least one of $R_1$, $R_2$, and $R_3$ is an $SiR_4,R_5,R_6$ group and that it is not one of the following compounds:

(E)-(5-(4-(trimethylsilyloxy)styryl)-1,3-phenylene)bis(oxy) bis(trimethylsilane), (E)-4-(3,5-bis(triisopropylsylyloxy)styryl)phenol, (E)-3-(tert-butyldimethylsilyloxy)-5-(4-(tert-butyldimethylsilyloxy)styryl)phenol, (E)-4-(3,5-bis(tert-butyldimethylsilyloxy)styryl)phenol, (E)-3-(tert-butyldimethylsilyloxy)-5-(4-hydroxystyryl)phenol, (E)-5-(4-(tert-butyldimethylsilyloxy)styryl)benzene-1,3-diol, (E)-(5-(4-(tert-butyldimethylsilyloxy)styryl)-1,3-phenylene)bis(oxy)bis(tert-butyldimethylsilane).

In a preferred embodiment, $R_1$ and $R_2$ are an $SiR_4R_5R_6$ group.

In a more preferred embodiment, $R_3$ is H.

In another more preferred embodiment, $R_3$ is —NH(CO)$R_7$.

In another more preferred embodiment, $R_3$ is the following carbohydrate:

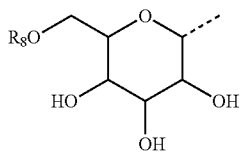

where $R_8$ is selected from among H or —C(O)—$R_9$, with $R_9$ being a $C_1$-$C_{22}$ alkyl group OR a $C_2$-$C_{22}$ alkenyl group.

In a more preferred embodiment, when $R_1$ and $R_2$ are an $SiR_4R_5R_6$ group, $R_4$ and $R_5$ are methyl, and $R_6$ is tert-butyl. In another more preferred embodiment, $R_4$, $R_5$, and $R_6$ are ethyl. In another more preferred embodiment, $R_4$, $R_5$, and $R_6$ are isopropyl.

In a preferred embodiment, $R_1$ and $R_3$ are an $SiR_4R_5R_6$ group.

In a more preferred embodiment, $R_2$ is H.

In another more preferred embodiment, $R_2$ is —NH(CO)$R_7$.

In another more preferred embodiment, $R_2$ is the following carbohydrate:

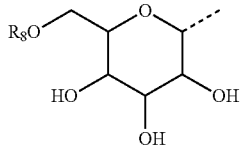

where $R_8$ is selected from among H or —C(O)—$R_9$, with $R_9$ being a $C_1$-$C_{22}$ alkyl group OR a $C_1$-$C_{22}$ alkenyl group.

In a more preferred embodiment, when $R_1$ and $R_3$ are an $SiR_4R_5R_6$ group, $R_4$ and $R_5$ are methyl, and $R_6$ is tert-butyl. In another more preferred embodiment, $R_4$, $R_5$, and $R_6$ are ethyl. In another more preferred embodiment, $R_4$, $R_5$, and $R_6$ are isopropyl.

In another more preferred embodiment, $R_1$, $R_2$ and $R_3$ are an $SiR_4R_5R_6$ group.

In a more preferred embodiment, when $R_1$, $R_2$, and $R_3$ are an $SiR_4R_5R_6$ group, $R_4$ and $R_5$ are methyl, and $R_6$ is tert-butyl. In another more preferred embodiment, $R_4$, $R_5$, and $R_6$ are ethyl. In another more preferred embodiment, $R_4$, $R_5$, and $R_6$ are isopropyl.

In another more preferred embodiment of the substituents that are the $SiR_4R_5R_6$ group, $R_4$ and $R_5$ are phenyl, and $R_6$ is tert-butyl. And in another more preferred embodiment, $R_4$, $R_5$, and $R_6$ are methyl.

In another preferred embodiment, the compound of formula (I') is selected from the following group:
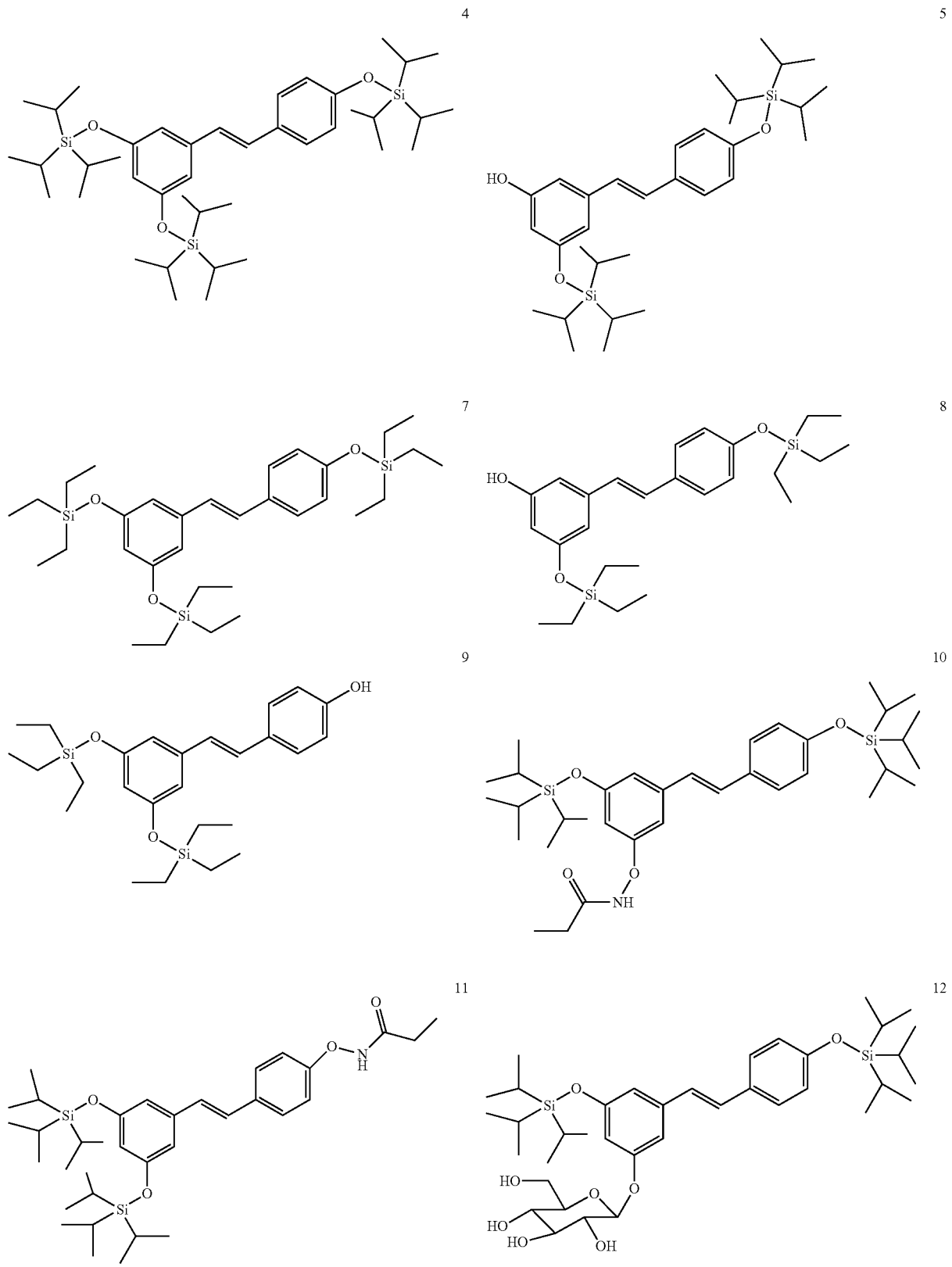

-continued
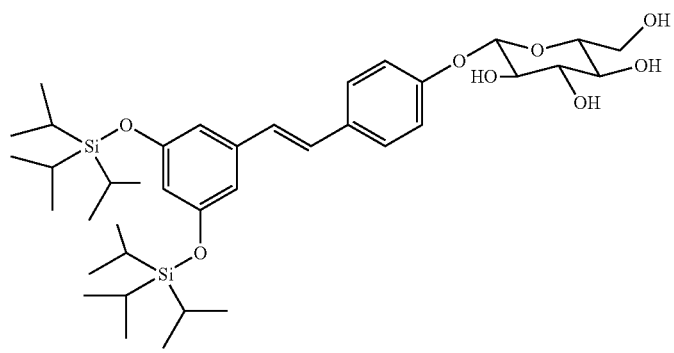
13
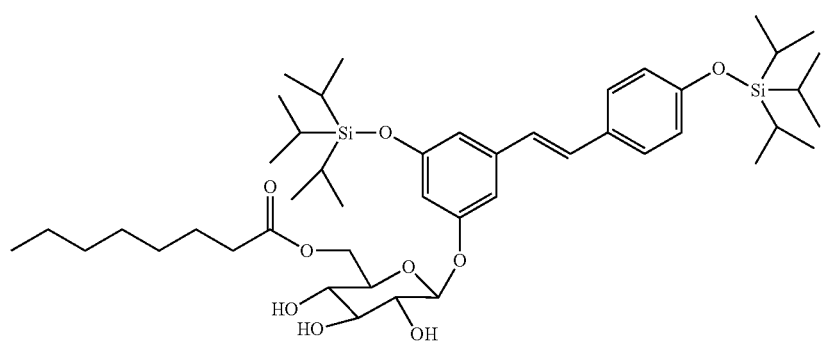
14
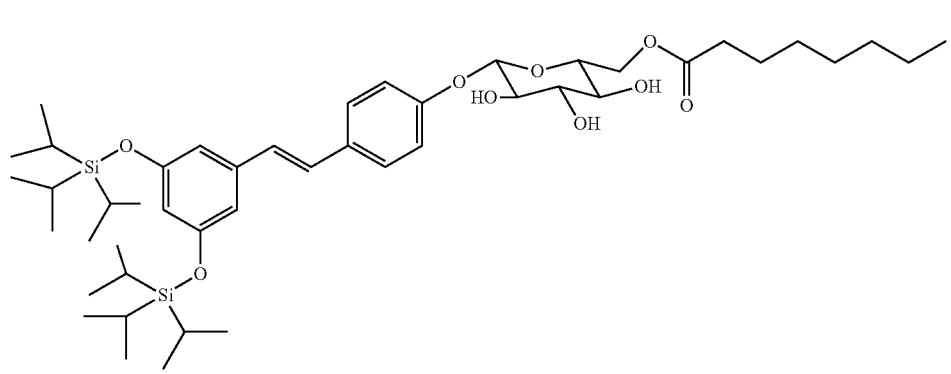
15
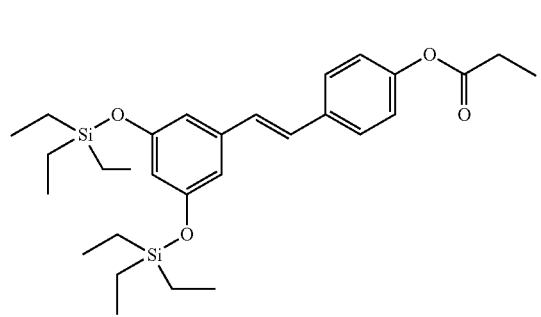
16
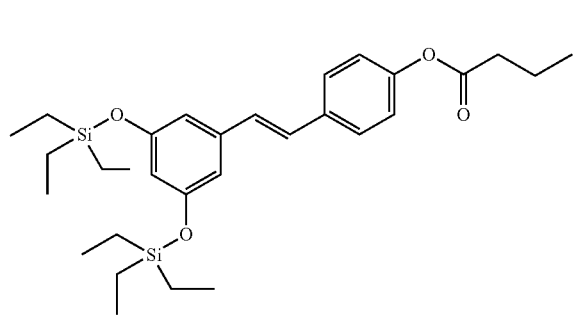
17
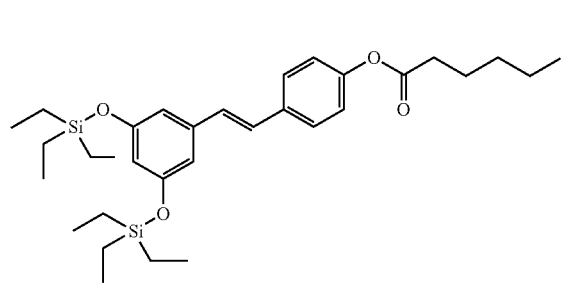
18
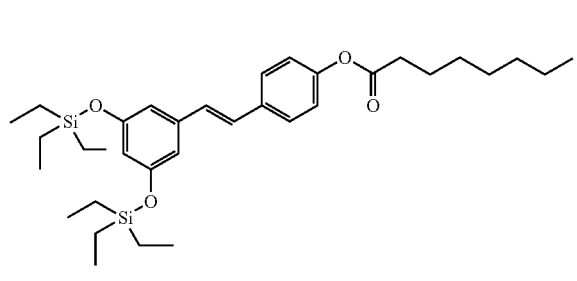
19

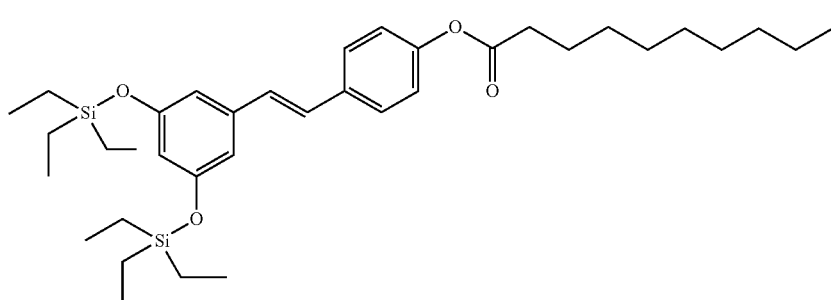

20

Another aspect of the invention relates to the use of the compound of formula (I') described above for the manufacture of a medicament.

Another aspect of the invention relates to a pharmaceutical composition comprising a compound of formula (I') as described above.

Another aspect of the invention relates to a method for treating an inflammatory, neurological, or neurodegenerative disease comprising the administration of a therapeutically effective amount of a compound of formula (I) or (I') to a patient in need thereof.

In the meaning used in this description, the term "therapeutically effective amount" refers to the amount of active compound that is sufficient to produce the desired effect in which the symptoms of the disease are attenuated. The dose should not be used in proportions that cause unwanted side effects the clinical evaluation of which makes them adverse and therapeutically untreatable. The dose will generally vary with the age, condition, sex, and extent of the disease in the patient as well as with the route and frequency of administration and can be determined on a case-by-case basis.

In the present invention, the term "alkyl" refers to linear or branched hydrocarbon chain radical having from 1 to 22, preferably from 1 to 12, and more preferably from 1 to 6 carbon atoms, and that bind to the rest of the molecule by a single bond, e.g., propyl, ethyl, methyl, isopropyl, undecanoyl, heptadecanoyl, octadecanoyl, etc. These alkyl radicals can be optionally substituted at one or more positions by one or more groups such as hydroxyl, amines, amides, oxo, cyano, halogens, aryl, etc.

In the present invention, the term "alkenyl" refers to unsaturated, linear, or branched aliphatic chains having from 2 to 22 carbon atoms and having between one and six unsaturations depending on the number of carbons, including but not limited to vinyl, allyl, oleyl, linoleyl, linolenyl, eicosapentaenoyl, docosahexaenoyl, etc. These alkyl radicals can be optionally substituted at one or more positions by one or more groups such as hydroxyl, amines, amides, oxo, cyano, halogens, aryl, etc.

The compounds of the present invention represented by the formula (I) and (I'), and more concretely the specific compounds belonging to this general formula described above, can include isomers, depending on the presence of multiple bonds (e.g., Z, E), including optical isomers or enantiomers, depending on the presence of chiral centers. The individual isomers, enantiomers, or diastereomers and mixtures thereof fall within the scope of the present invention. The individual enantiomers or diastereomers, as well as mixtures thereof, can be separated using conventional techniques.

The compounds of the invention can be in crystalline form as free compounds or as solvates, and both forms are intended to be within the scope of the present invention. In this sense, the term "solvate," as used herein, includes both pharmaceutically acceptable solvates, i.e., solvates of the compound of formula (I) or (I') that can be used in the manufacture of a medicament as pharmaceutically unacceptable solvates that may be useful in the preparation of pharmaceutically acceptable solvates or salts. The nature of the pharmaceutically acceptable solvate is not critical as long as it is pharmaceutically acceptable. In a particular embodiment, the solvate is a hydrate. The solvates can be obtained by conventional solvation methods that are well known to those skilled in the art.

For use in therapy, the compounds of formula (I) or (I'), their isomers, salts, or solvates, are preferably in a pharmaceutically acceptable or substantially pure form—that is, they have a pharmaceutically acceptable level of purity excluding the normal pharmaceutical additives such as diluents and carriers, and not including material that is considered toxic at normal dosing levels. The levels of purity for the active substance are preferably greater than 50%, more preferably greater than 70%, even more preferably greater than 90%. In a preferred embodiment, the levels of the compound of formula (I) or (I') or salts or solvates thereof are greater than 95%.

Unless otherwise indicated, the compounds of the invention also include compounds that differ only through the presence of one or more isotopically enriched atoms. For example, compounds having said structure, with the exception of the substitution of a hydrogen by a deuterium or by tritium, or the substitution of a carbon by a $^{13}$C- or $^{14}$C-enriched carbon or a $^{15}$N-enriched nitrogen, lie within the scope of this invention.

The compounds of formula (I) or (I') for therapeutic use are prepared in solid form or as an aqueous suspension in a pharmaceutically acceptable diluent. These preparations can be administered by any appropriate route of administration, for which purpose the preparation will be formulated in the pharmaceutical form that is appropriate for the selected route of administration. For example, the compounds of formula (I) or (I') will be combined with excipients such as starch or lactose or adjuvants such as cyclodextrins as well as any type of pharmaceutical carrier known to a person skilled in the art for the preparation of solid or liquid formulations. In a particular embodiment, the administration of the compound of formula (I) or (I') provided by this invention is carried out orally, topically, rectally, or parenterally (including subcutaneously, intraperitoneally, intradermally, intramuscularly, intravenously, etc.). A review of the different pharmaceutical forms of drug administration and of the excipients necessary for obtaining them can be found, for example, in the "Tratado de Farmacia Galénica" ["Treatise on Galenic Pharmacy"], C. Faulí i Trillo, 1993, Luzán 5, S. A. Ediciones, Madrid, or in other customary or similar publications of the Spanish, European, or United States Pharmacopoeias.

The compounds described in the present invention and the pharmaceutically acceptable salts and solvates thereof, as well as the pharmaceutical compositions containing them, can be used in conjunction with other, additional drugs in order to provide combination therapy. These additional drugs can be part of the same pharmaceutical composition or, alternatively, they can be provided in the form of a separate composition for simultaneous or non-simultaneous administration with that of the pharmaceutical composition comprising a compound of formula (I) or (I'), or an isomer, solvate, or a pharmaceutically acceptable salt thereof.

Throughout the description and the claims, the expression "comprises" and variants thereof are not intended to exclude other technical features, additives, components, or steps. For those skilled in the art, other objects, advantages, and features of the invention will be apparent in part from the description and in part from the practicing of the invention. The following examples and figures are provided for the sake of illustration and are not intended to limit the scope of the present invention.

EXAMPLES

Figure 1:
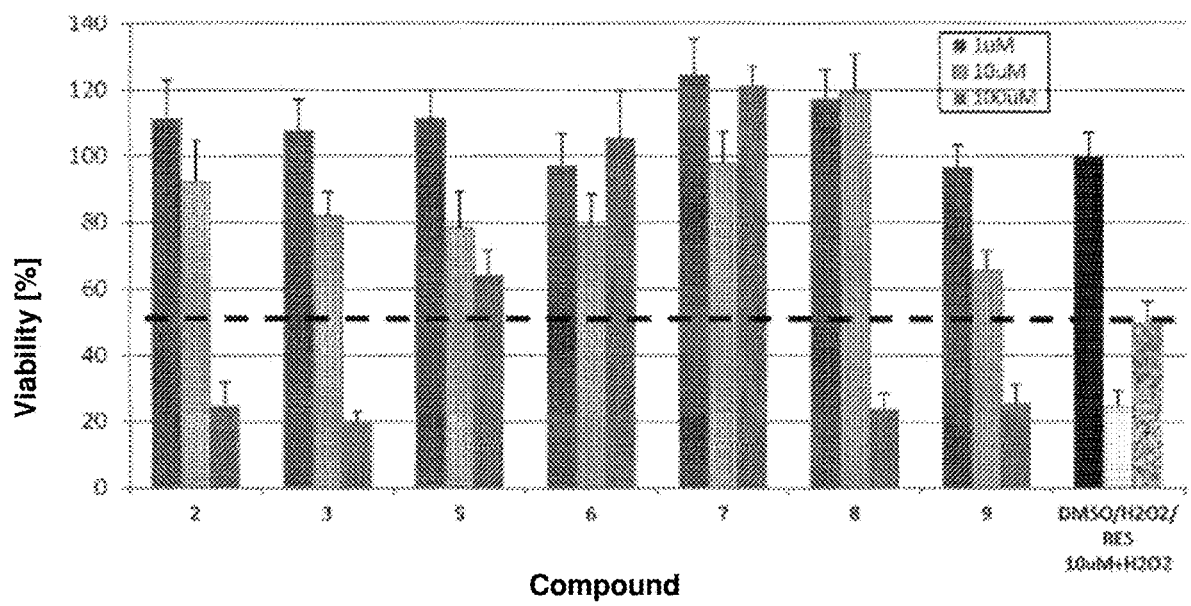
FIG. 1. Cell viability in neuroblastoma SH-SY5Y after damage with $H_2O_2$ and treatment with the different compounds 2-9. The controls are DMSO: 1% DMSO; $H_2O_2$: $H_2O_2$ in 1% DMSO; RES 10 µM+$H_2O_2$: resveratrol in $H_2O_2$ in 1% DMSO.
Figure 2:
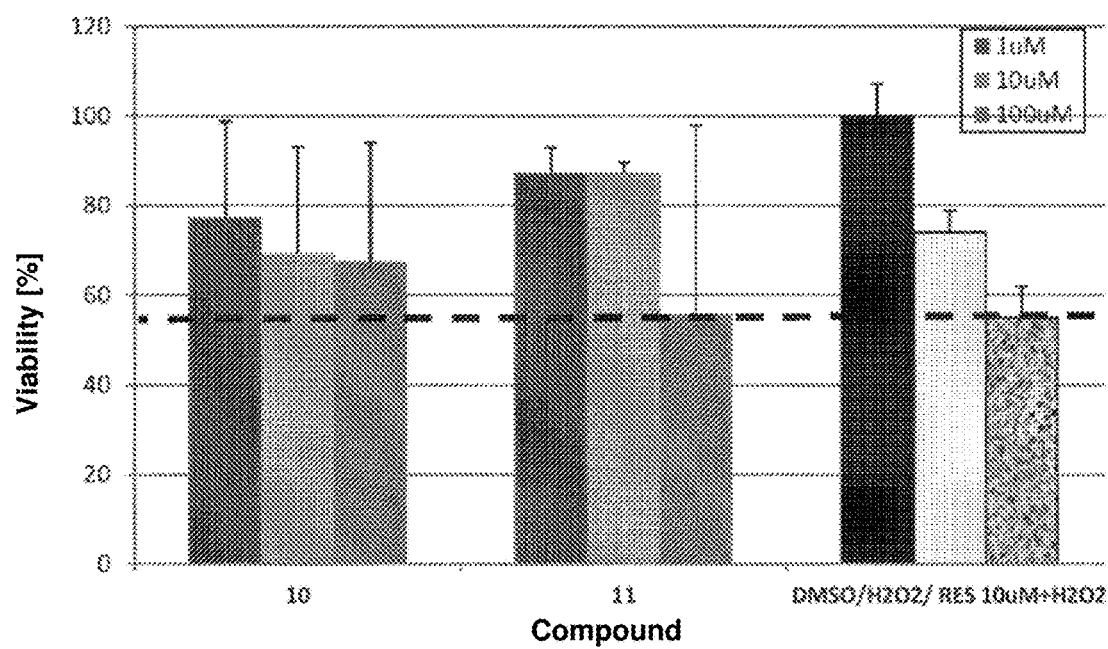
FIG. 2. Cell viability in neuroblastoma SH-SY5Y after damage with $H_2O_2$ and treatment with the different compounds 10-11. The controls are DMSO: 1% DMSO; $H_2O_2$: $H_2O_2$ in 1% DMSO; RES 10 µM+$H_2O_2$: resveratrol in $H_2O_2$ in 1% DMSO.
Figure 3:
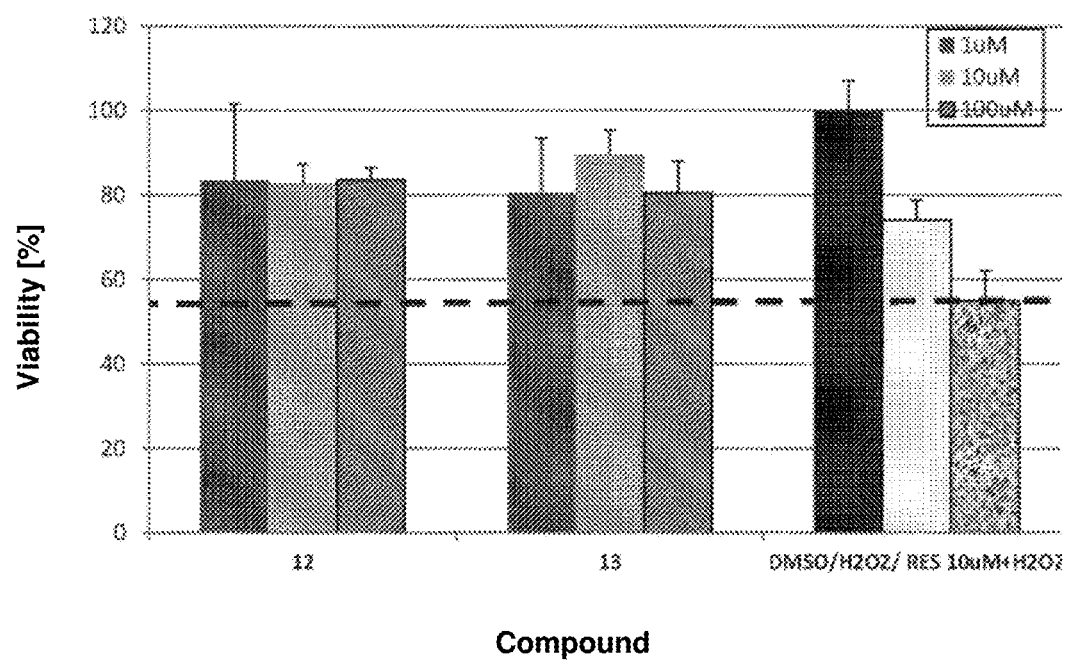
FIG. 3. Cell viability in neuroblastoma SH-SY5Y after damage with $H_2O_2$ and treatment with the different compounds 12-13. The controls are DMSO: 1% DMSO; $H_2O_2$: $H_2O_2$ in 1% DMSO; RES 10 µM+$H_2O_2$: resveratrol in $H_2O_2$ in 1% DMSO.
Figure 4:
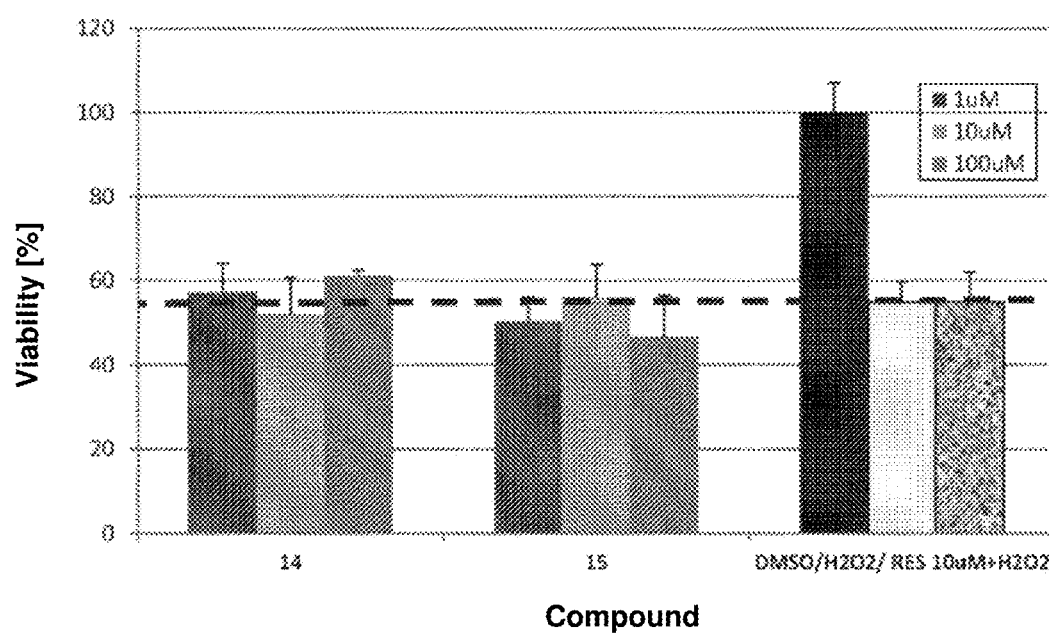
FIG. 4. Cell viability in neuroblastoma SH-SY5Y after damage with $H_2O_2$ and treatment with the different compounds 14-15. The controls are DMSO: 1% DMSO; $H_2O_2$: $H_2O_2$ in 1% DMSO; RES 10 µM+$H_2O_2$: resveratrol in $H_2O_2$ in 1% DMSO.
Figure 5:
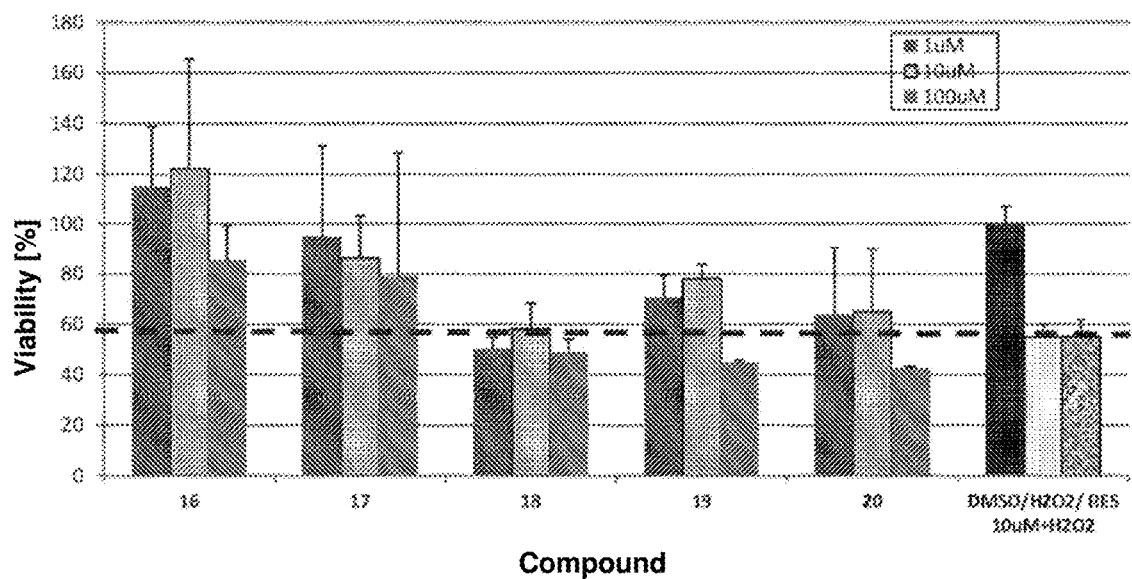
FIG. 5. Cell viability in neuroblastoma SH-SY5Y after damage with $H_2O_2$ and treatment with the different compounds 16-20. The controls are DMSO: 1% DMSO; $H_2O_2$: $H_2O_2$ in 1% DMSO; RES 10 µM+$H_2O_2$: resveratrol in $H_2O_2$ in 1% DMSO.
Figure 6:
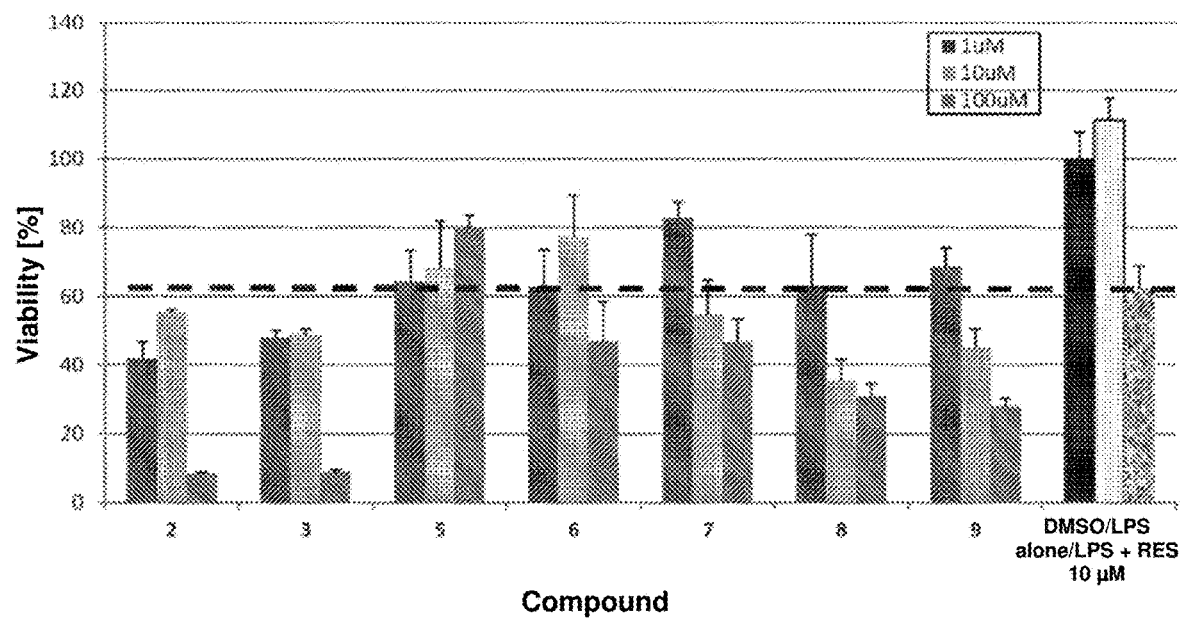
FIG. 6. Cell viability in RAW macrophages after inflammation produced with LPS and treatment with the different compounds 2-9. The controls are DMSO: 1% DMSO; LPS alone: LPS (100 ng/ml); LPS+RES 10 µM: LPS (100 ng/ml)+resveratrol.
Figure 7:
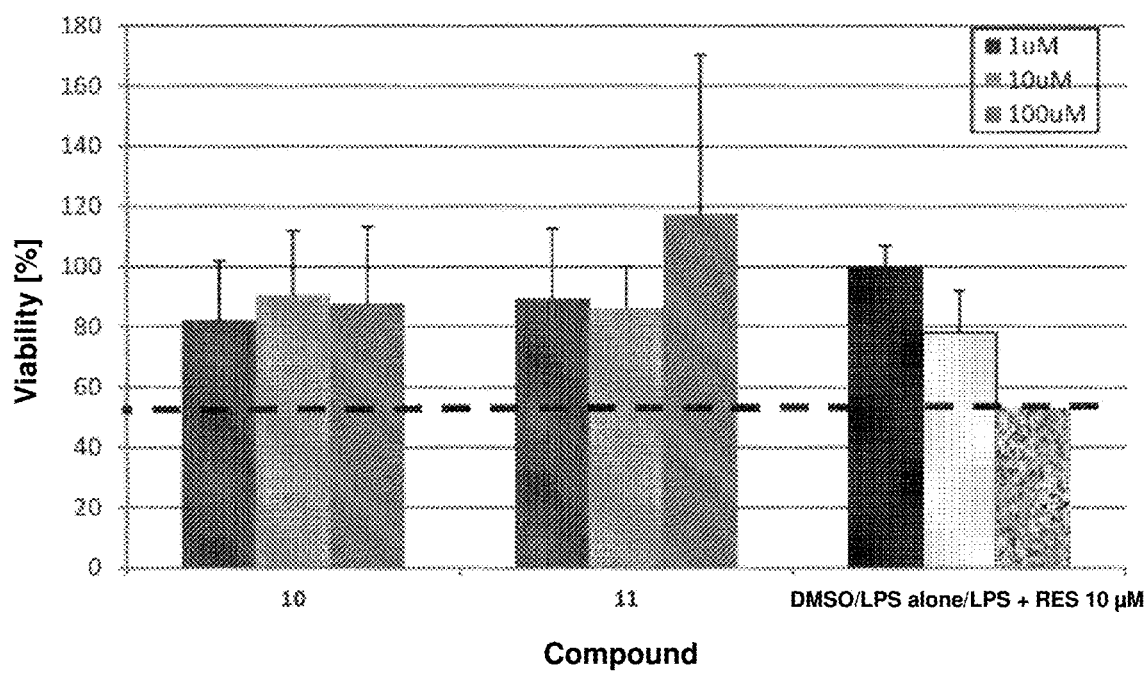
FIG. 7. Cell viability in RAW macrophages after inflammation produced with LPS and treatment with the different compounds 10-11. The controls are DMSO: 1% DMSO; LPS alone: LPS (100 ng/ml); LPS+RES 10 µM: LPS (100 ng/ml)+resveratrol.
Figure 8:
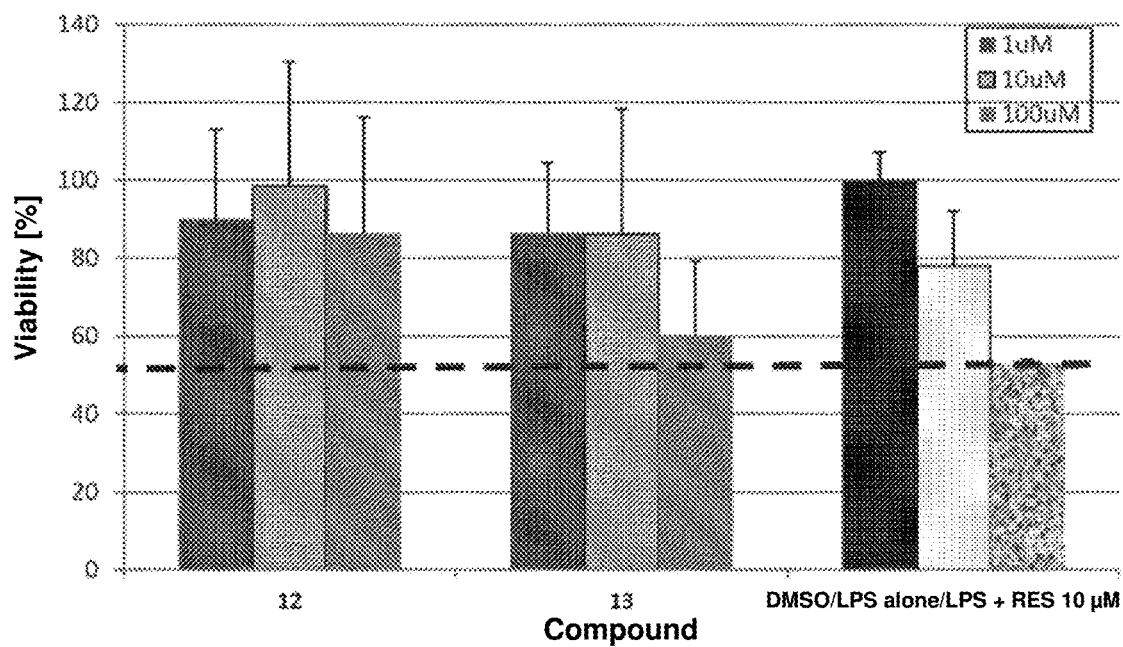
FIG. 8. Cell viability in RAW macrophages after inflammation produced with LPS and treatment with the different compounds 12-13. The controls are DMSO: 1% DMSO; LPS alone: LPS (100 ng/ml); LPS+RES 10 µM: LPS (100 ng/ml)+resveratrol.
Figure 9:
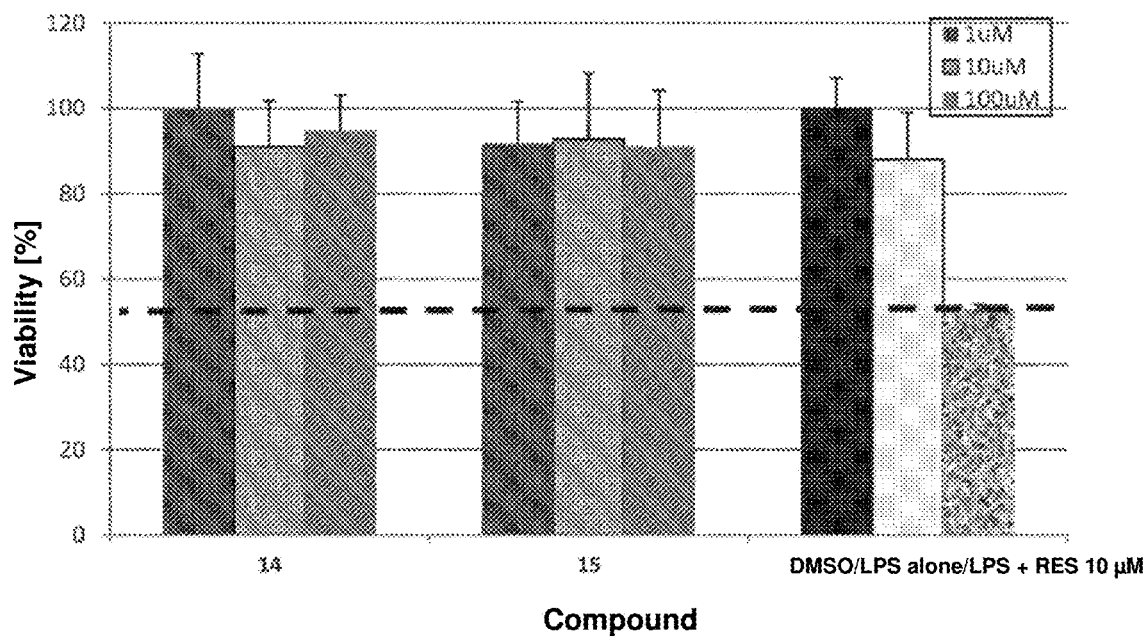
FIG. 9. Cell viability in RAW macrophages after inflammation produced with LPS and treatment with the different compounds 14-15. The controls are DMSO: 1% DMSO; LPS alone: LPS (100 ng/ml); LPS+RES 10 µM: LPS (100 ng/ml)+resveratrol.
Figure 10:
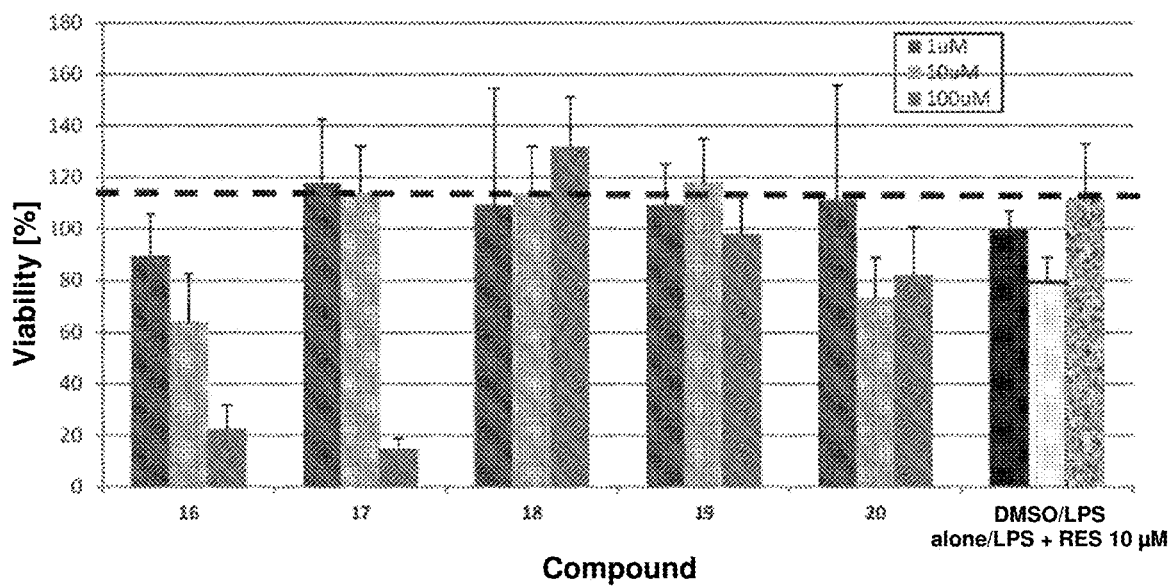
FIG. 10. Cell viability in RAW macrophages after inflammation produced with LPS and treatment with the different compounds 16-20. The controls are DMSO: 1% DMSO; LPS alone: LPS (100 ng/ml); LPS+RES 10 µM: LPS (100 ng/ml)+resveratrol.

The invention will be illustrated below by means of tests conducted by the inventors that demonstrate the effectiveness of the product of the invention.

Example 1: Synthesis of the Silylated Derivatives of Resveratrol

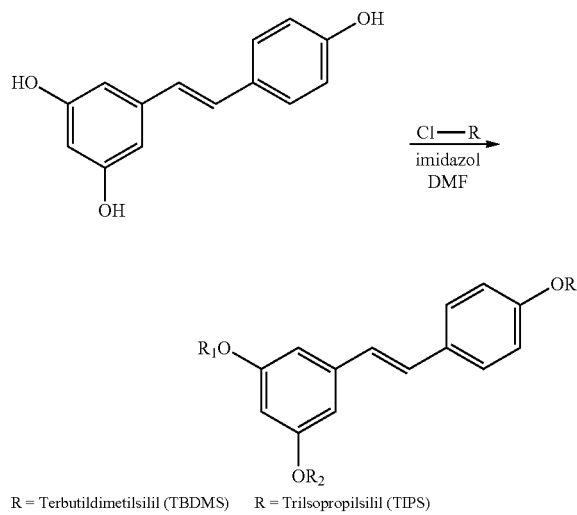

R = Terbutildimetilsilil (TBDMS)  R = Triisopropilsilil (TIPS)
1: $R_1 = R_2 = R_3$ = TBDMS       4: $R_1 = R_2 = R_3$ = TIPS
2: $R_1 = R_3$ = TBDMS; $R_2$ = H  5: $R_1 = R_3$ = TIPS; $R_2$ = H
3: $R_1 = R_2$ = TBDMS; $R_3$ = H  6: $R_1 = R_2$ = TIPS; $R_3$ = H R = Trietilsilis (TES)
7: $R_1 = R_2 = R_3$ = TES
8: $R_1 = R_3$ = TES; $R_2$ = H
9: $R_1 = R_2$ = TES; $R_3$ = H

General Method of Silylation.

Resveratrol (1 eq.) and imidazole (2.5 eq.) were added to a round-bottom flask with DMF (3 ml/mmol resveratrol) under stirring and cooled to 0° C. The corresponding silyl chloride (1, 4-1, 55 eq.) was then added dropwise in two batches, the first half at=0 h and the second half at=3 h. The reaction was stirred for a total of 6 h at room temperature. The reaction mixture was then filtered, diluted in water, and extracted with ethyl acetate (3×20 ml). The combined organic phases were dried with $MgSO_4$, filtered, concentrated to dryness, and purified by silica gel column chromatography, with elution being performed with hexane/ethyl acetate mixtures.

Series of Tert-Butyldimethylsilyl Resveratrol Derivatives.

Following the general method, resveratrol (830 mg, 3.64 mmol) and tert-butyldimethylsilyl chloride (849.55 mg, 5.64 mmol) were used to obtain compounds 1, 2, and 3 in addition to the monosilylated derivatives after purifying the reaction mixture by column chromatography using a gradient of hexane/ethyl acetate (8:1 to 2:1).

3,4',5-O-tri-tert-butyldimethylsilyl resveratrol, compound 1. Yield=5.8%; $R_f$=0.9 (hexane:ethyl acetate—7:3).

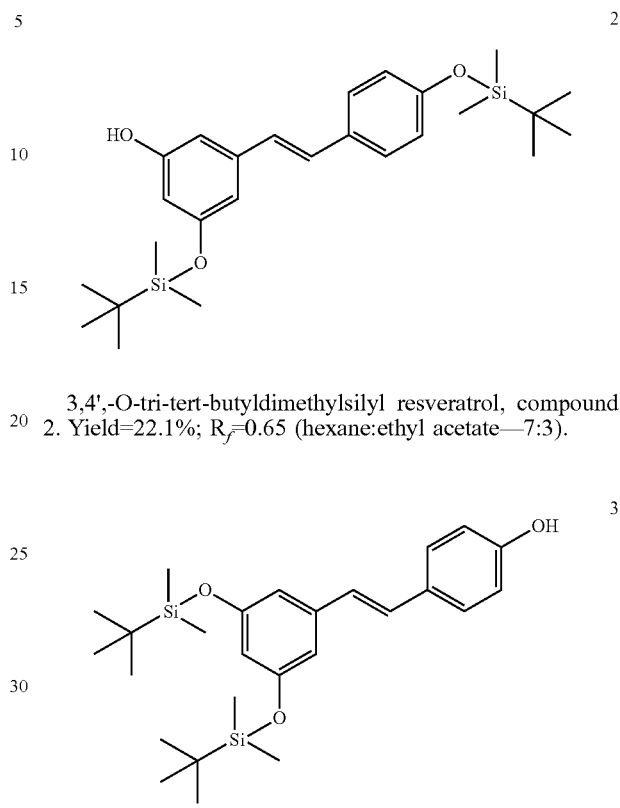

3,4',-O-tri-tert-butyldimethylsilyl resveratrol, compound 2. Yield=22.1%; $R_f$=0.65 (hexane:ethyl acetate—7:3).

3,5,-O-tri-tert-butyldimethylsilyl resveratrol, compound 3. Yield=6.4%; $R_f$=0.55 (hexane:ethyl acetate—7:3).

Series of Triisopropylsilyl Resveratrol Derivatives.

Following the general method, resveratrol (816 mg, 3.57 mmol) and triisopropylsilyl chloride (1.19, 5.54 mmol) were used to obtain compounds 4, 5, and 6 in addition to the monosilylated derivatives after purifying the reaction mixture by column chromatography using a gradient of hexane/ethyl acetate (10:1 to 1:1).

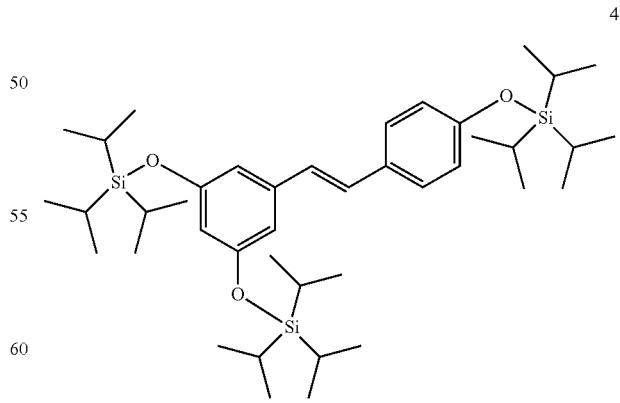

3,4',5-O-tri-triisopropylsilyl resveratrol, compound 4. Yield=19.4%; $R_f$=0.9 (hexane:ethyl acetate—3:1). RMN of $^1$H (400 MHz, $CDCl_3$): δ=7.47 (d, J=8.3 Hz, 2H), 7.05 (d, J=16.2 Hz, 1H, CH), 6.95 (dd, J=12.4, 6.4 Hz, 3H, CH and H), 6.74 (s, 2H, H² and H⁶), 6.44 (s, 1H, H⁴), 1.41-1.33 (m, 9H, CH—Si), 1.29-1.16 (m, 54H, CH₃). RMN of $^{13}$C (101 MHz, CDCl₃): δ=157.10, 155.96, 139.44, 130.45, 128.39, 127.73, 126.83, 120.17, 111.26, 110.94, 18.02, 12.78.

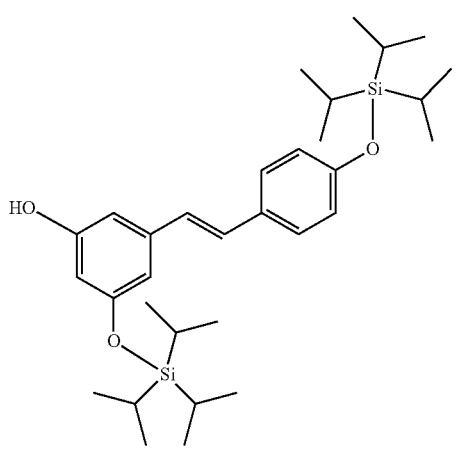

3,4',-O-di-triisopropylsilyl resveratrol, compound 5. Yield=26.1%; $R_f$=0.65 (hexane:ethyl acetate—3:1). RMN of $^1$H (400 MHz, CDCl₃): b=7.34 (d, J=8.2 Hz, 2H), 6.96 (d, J=16.2 Hz, 1H), 6.83 (t, J=12.0 Hz, 3H), 6.64 (s, 1H), 6.55 (s, 1H), 6.33 (s, 1H), 1.30-1.22 (m, 6H), 1.11 (dd, J=16.0, 7.4 Hz, 36H). RMN of $^{13}$C (101 MHz, CDCl₃): δ=158.14, 157.12, 155.68, 139.63, 130.56, 127.98, 127.47, 126.57, 119.77, 109.57, 106.15, 106.06, 17.40, 17.37, 17.10, 12.62, 12.59, 12.32. TOF MS-ES, calculated mass: C₃₂H₅₁O₃Si₂ [M−H]=539.3377, measured mass: [M−H]=539.3390.

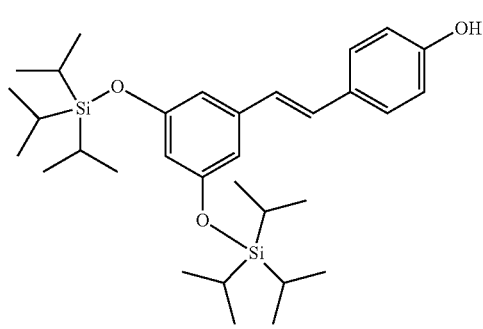

3,5,-O-di-triisopropylsilyl resveratrol, compound 6. Yield=8.7%; $R_f$=0.5 (hexane:ethyl acetate—3:1).

Series of Triethylsilyl Resveratrol Derivatives.

Following the general method, resveratrol (809 mg, 3.54 mmol) and ethylsilyl chloride (1.19, 5.49 mmol) were used to obtain compounds 7, 8, and 9 in addition to the monosilylated derivatives after purifying the reaction mixture by column chromatography using a gradient of hexane/ethyl acetate (10:1 to 1:1).

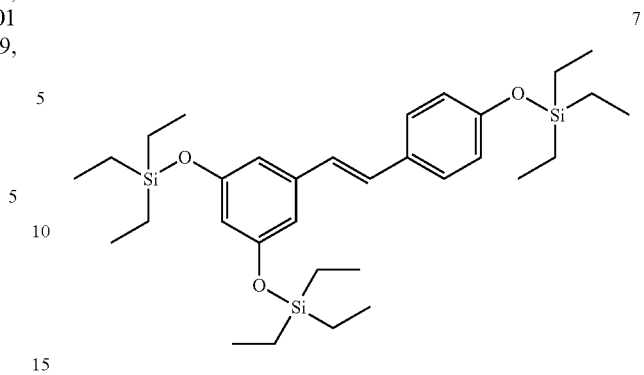

3,4',5-O-tri-triethylsilyl resveratrol, compound 7. Yield=3.8%; $R_f$=0.95 (hexane:ethyl acetate—3:1). RMN of $^1$H (400 MHz, CDCl₃): δ=7.40 (d, J=8.5 Hz, 2H), 6.98 (d, J=16.2 Hz, 1H), 6.90-6.82 (m, 3H), 6.64 (d, J=2.0 Hz, 2H), 6.31 (t, J=2.0 Hz, 1H), 1.04 (td, J=7.8, 2.8 Hz, 26H), 0.78 (q, J=7.9 Hz, 18H). RMN of $^{13}$C (101 MHz, CDCl₃): =156.61, 155.45, 139.48, 130.60, 128.44, 127.73, 126.76, 120.17, 111.41, 110.93, 6.66, 5.03. Calculated mass: C₃₂H₅₅O₃Si₃ [M+H]=571.3459, measured mass: [M+H]=571.3460.

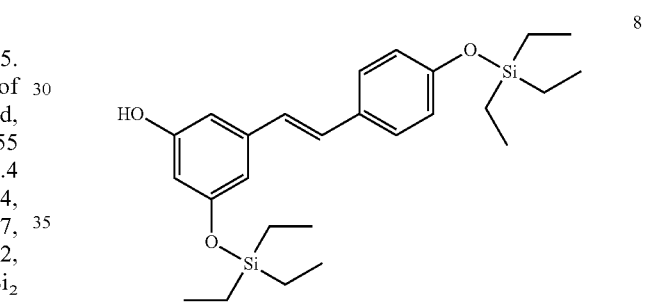

3,4',-O-tri-triethylsilyl resveratrol, compound 8. Yield=14.9%; $R_f$=0.6 (hexane:ethyl acetate—3:1). RMN of $^1$H (400 MHz, CDCl₃): δ=7.40 (d, J=8.6 Hz, 2H), 6.98 (d, J=16.2 Hz, 1H), 6.91-6.82 (m, 3H), 6.62 (s, 1H), 6.61 (s, 1H), 6.32 (s, 1H), 1.09-1.02 (m, 18H), 0.80 (q, J=7.9 Hz, 12H). RMN of $^{13}$C (101 MHz, CDCl₃): δ=156.92, 156.69, 155.45, 139.94, 130.58, 128.82, 127.83, 126.47, 120.25, 110.96, 106.52, 106.40, 6.67, 6.64, 5.03. TOF MS-ES⁺, calculated mass: C₂₆H₄₁O₃Si₂ [M+H]=457.2594, measured mass: [M+H]=457.2593.

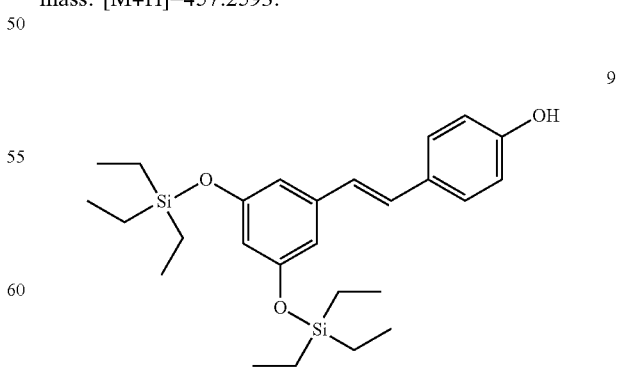

3,5,-O-tri-triethylsilyl resveratrol, compound 9. Yield=6.8%; $R_f$=0.5 (hexane:ethyl acetate—3:1). RMN of $^1$H (400 MHz, CDCl₃): 7.37 (d, J=8.3 Hz, 2H), 6.96 (d, J=16.2 Hz, 1H), 6.82 (t, J=12.6 Hz, 3H), 6.63 (s, 2H), 6.25 (s, 1H), 1.02 (t, J=7.9 Hz, 18H), 0.76 (q, J=7.9 Hz, 12H). RMN of $^{13}$C (101 MHz, CDCl$_3$): δ=157.11, 156.55, 140.04, 128.84, 128.66, 127.64, 127.55, 125.16, 115.19, 110.99, 110.08, 48.34, 48.13, 47.92, 47.70, 47.49, 47.28, 47.06, 5.77, 4.66. TOF MS-ES$^+$, calculated mass: C$_{26}$H$_{41}$O$_3$Si$_2$ [M+H]=457.2594, measured mass: [M+H]=457.2586.

Series of Triisopropylsilyl and Ethyl Carbamide Resveratrol Derivatives.

Ethyl isocyanate (1.5 eq.) and triethylamine (2 eq.) were added to a solution of 3,4'-dithiisopropylsilyl resveratrol or 3,5-dithiisopropylsilyl resveratrol (1 eq.) in dichloromethane. After 1 h of reaction at room temperature, the reaction was concentrated and purified on a chromatography column, with elution being performed with hexane:ethyl acetate (from 2:1 to 0:1).

10

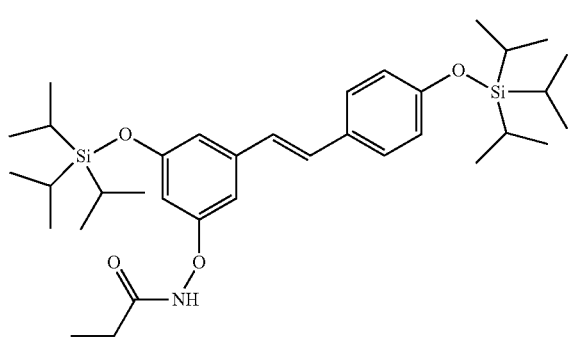

3,4',-O-ditriisopropylsilyl-5-ethyl carbamate resveratrol, compound 10. Yield=80.2%. R$_f$=0.9 (hexane:ethyl acetate—5:1). RMN of $^1$H (300 MHz, CDCl$_3$): δ=7.39 (d, J=8.5 Hz, 2H), 7.02 (d, J=16.2 Hz, 1H), 6.89 (dd, J=14.6, 5.9 Hz, 5H), 6.60 (s, 1H), 3.40-3.26 (m, 2H), 1.30 (ddd, J=10.6, 7.4, 3.7 Hz, 9H), 1.15 (dd, J=7.0, 3.1 Hz, 36H). RMN of $^{13}$C (75 MHz, CDCl$_3$): δ=157.04, 156.29, 152.30, 139.75, 130.38, 129.38, 128.01, 126.25, 120.39, 115.12, 112.30, 36.38, 18.21, 18.18, 17.97, 15.40, 12.95, 12.93, 12.57. TOF MS-ES$^+$, calculated mass: C$_{35}$H$_{57}$NO$_4$Si$_2$ [M+H]=612.3904, measured mass: [M+H]=612.3907.

11

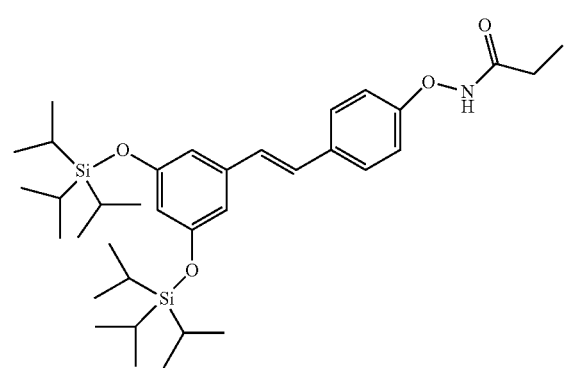

3,5-O-ditriisopropylsilyl-4-ethyl carbamate resveratrol, compound 11. Yield=85.6%. R$_f$=0.9 (hexane:ethyl acetate—5:1). RMN of $^1$H (300 MHz, CDCl$_3$): δ=7.51 (d, J=8.0 Hz, 2H), 7.15 (d, J=8.0 Hz, 2H), 7.01 (d, J=16.4 Hz, 1H), 6.93 (d, J=16.1 Hz, 1H), 6.67 (s, 2H), 6.38 (s, 1H), 3.41-3.28 (m, 2H), 1.32-1.22 (m, 9H), 1.15 (d, J=7.2 Hz, 36H). RMN of $^{13}$C (75 MHz, CDCl$_3$): δ=157.31, 157.25, 139.15, 128.14, 128.00, 127.59, 121.99, 116.20, 116.04, 112.17, 111.61, 111.38, 45.95, 36.41, 18.20, 12.95. TOF MS-ES$^+$, calculated mass: C$_{35}$H$_{57}$NO$_4$Si$_2$ [M+H]=612.3904, measured mass: [M+H]=612.3900.

Series of Triisopropylsilyl Glucosyl Resveratrol Derivatives.

Under stirring and an inert argon atmosphere, 3,4'-ditriisopropylsilyl resveratrol or 3,5-ditriisopropylsilyl resveratrol (1 eq.) was dissolved in 15 ml of anhydrous dichloromethane and peracetyl glucose trifluoroacetimidate (1.5 eq.) and boron trifluoride etherate (0.1 eq.) were added. After 30 min of reaction, 5 ml of triethylamine was added, concentrated, and added to a silica gel purification column, with elution being performed with a mixture of hexane and ethyl acetate (5:1). The obtained product was dissolved in a mixture of dichloromethane, water, and methanol (5 ml, 2:1:2), and sodium bicarbonate (3 eq.) was added. After deprotection of the acetate units of the glucose unit (24-48 h), the reaction was concentrated and purified by column chromatography, with elution being performed with hexane:ethyl acetate (from 1:1 to 1:3).

12

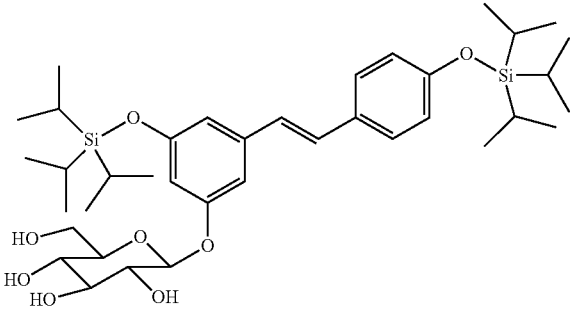

3,4'-O-ditriisopropylsilyl-5-glucosyl resveratrol, compound 12. Yield=70.6%. R$_f$=0.05 (hexane:ethyl acetate—1:3). RMN of $^1$H (500 MHz, CD$_3$OD): δ=7.43 (d, J=8.6 Hz, 2H), 7.05 (d, J=16.3 Hz, 1H), 6.98-6.89 (m, 2H), 6.87 (d, J=8.6 Hz, 2H), 6.70 (s, 1H), 6.55 (t, J=2.0 Hz, 1H), 4.92-4.88 (m, 1H), 3.94-3.88 (m, 1H), 3.75 (dd, J=11.9, 4.8 Hz, 1H), 3.52-3.38 (m, 4H), 1.36-1.23 (m, 6H), 1.18-1.10 (m, 36H). RMN of $^{13}$C (126 MHz, CD$_3$OD): δ=158.94, 156.93, 155.80, 139.83, 130.51, 128.55, 127.51, 126.04, 119.69, 111.96, 107.30, 107.07, 101.13, 76.86, 76.59, 73.48, 69.90, 61.01, 17.05, 16.99, 12.53, 12.51. TOF MS-ES$^+$, calculated mass: C$_{38}$H$_{62}$O$_8$Si$_2$ [M+Na]=725.3881, measured mass: [M+Na]=725.3682.

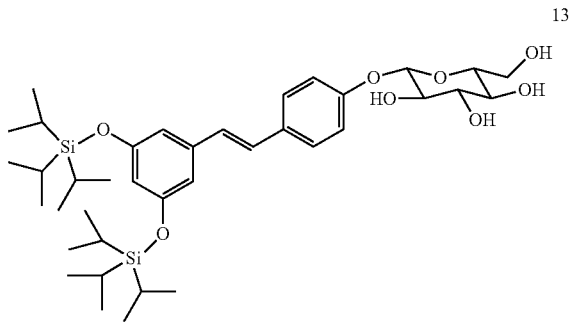 [SMILES: CC(C)[Si](Oc1cc(/C=C/c2ccc(OC3OC(CO)C(O)C(O)C3O)cc2)cc(O[Si](C(C)C)(C(C)C)C(C)C)c1)(C(C)C)C(C)C]

3,5-O-ditriisopropylsilyl-4'-glucosyl resveratrol, compound 13. Yield=75.3%. $R_f$=0.05 (hexane:ethyl acetate—1:3). RMN of $^1$H (500 MHz, CD$_3$OD): δ=7.48 (d, J=8.7 Hz, 2H), 7.09 (d, J=8.7 Hz, 2H), 6.95 (q, J=16.3 Hz, 3H), 6.66 (d, J=2.0 Hz, 2H), 6.32 (t, J=2.1 Hz, 1H), 4.96-4.90 (m, 1H), 3.91 (dd, J=12.1, 1.9 Hz, 1H), 3.73 (dd, J=12.1, 5.3 Hz, 1H), 3.51-3.47 (m, 2H), 3.45 (dd, J=5.0, 1.7 Hz, 1H), 3.44-3.38 (m, 1H), 1.31-1.23 (m, 6H), 1.14 (d, J=7.3 Hz, 36H). RMN of $^{13}$C (126 MHz, CD$_3$OD): δ=157.41, 156.96, 139.63, 131.54, 128.05, 127.37, 126.65, 116.54, 110.93, 110.28, 100.83, 76.75, 76.57, 73.49, 69.94, 61.10, 17.05, 12.55. TOF MS-ES$^+$, calculated mass: C$_{38}$H$_{62}$O$_8$Si$_2$ [M+Na]=725.3881, measured mass: [M+Na]=725.3907.

Series of Triisopropylsilyl Octanoyl-Glucosyl Resveratrol Derivatives.

3,4'-O-ditriisopropylsilyl-5-glucosyl resveratrol or 3,5-O-dithiisopropylsilyl-4'-glucosyl resveratrol (1 eq.) was dissolved in methyl tert-butyl ether and vinyl octanoate (3 eq.) and the enzyme Lypozyme TL IM® (same amount in grams as the resveratrol derivative). After 3 days of reaction, the enzyme was filtered and washed with ethyl acetate and methanol. After concentration of the solvent, it was purified by chromatography on a silica column, with elution being performed with hexane:ethyl acetate (from 2:1 to 1:3).

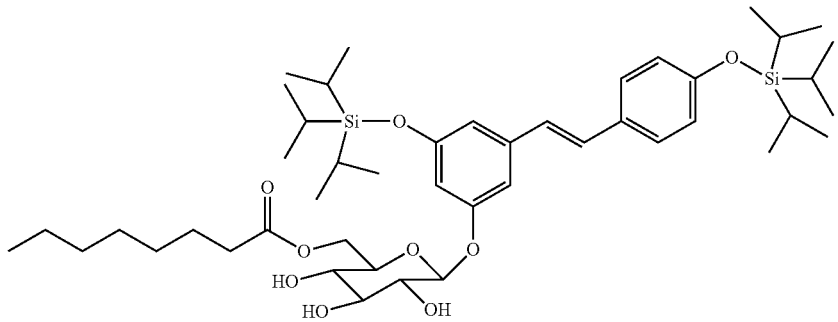

3,4'-O-ditriisopropylsilyl-5-(-6-octanoyl)glucosyl resveratrol, compound 14. Yield=75.3%. $R_f$=0.05 (hexane:ethyl acetate—1:3). RMN of $^1$H (500 MHz, CDCl$_3$): =$^1$H NMR (500 MHz, CdCl$_3$) δ=7.37 (d, J=8.5 Hz, 2H), 7.12 (d, J=8.5 Hz, 1H), 6.98 (d, J=16.1 Hz, 2H), 6.87 (d, J=8.5 Hz, 2H), 6.75 (s, 1H), 6.73 (s, 1H), 4.94-4.87 (m, 1H), 4.75-4.70 (m, 1H), 4.59-4.48 (m, 2H), 3.69-3.60 (m, 3H), 1.28-1.25 (m, 18H), 1.15-1.07 (m, 36H), 0.91-0.89 (m, 3H). RMN of $^{13}$C (126 MHz, CDCl$_3$): δ=171.07, 139.75, 130.16, 127.72, 126.19, 120.16, 119.68, 115.09, 112.90, 109.58, 107.50, 106.00, 104.78, 102.13, 100.89, 66.80, 60.38, 45.71, 38.73, 34.00, 31.91, 30.40, 29.69, 29.35, 28.91, 24.47, 23.78, 22.68, 21.03, 20.82, 17.94, 17.89, 17.86, 14.18, 14.10, 12.67, 12.62, 12.54, 10.96, 8.76. TOF MS-ES−, calculated mass: C$_{46}$H$_{76}$O$_9$Si$_2$ [M−H]=827.4950, measured mass: [M−H]=827.4922.

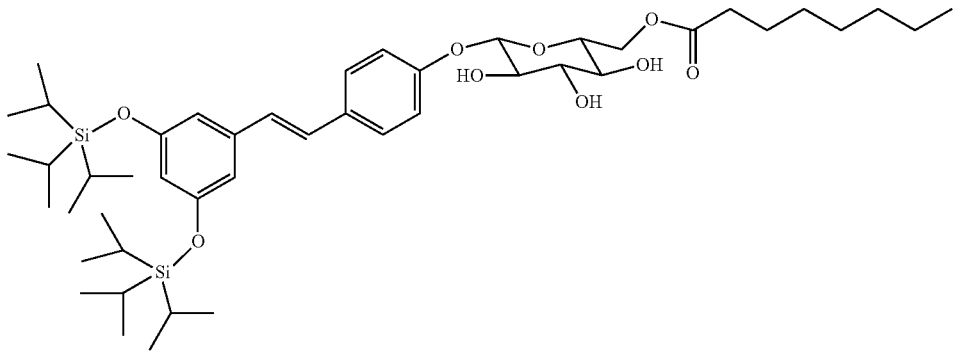

3,5-O-ditriisopropylsilyl-4'-(6-octanoyl)glucosyl resveratrol, compound 15. Yield=15.5%. $R_f$=0.07 (hexane:ethyl acetate—1:2). RMN of $^1$H (300 MHz, CDCl$_3$): δ 7.45 (d, J=8.5 Hz, 2H), 7.07 (d, J=8.4 Hz, 2H), 6.93 (q, J=16.2 Hz, 2H), 6.66 (s, 2H), 6.37 (s, 1H), 4.96 (d, J=6.0 Hz, 1H), 4.43 (m, 2H), 3.77-3.55 (m, 4H), 2.36 (t, J=7.5 Hz, 2H), 1.63 (d, J=6.8 Hz, 2H), 1.29-1.24 (m, 8H), 1.14 (d, J=7.0 Hz, 36H), 0.92-0.84 (m, 3H). RMN of $^{13}$C (75 MHz, CDCl$_3$): δ=174.78, 157.28, 139.28, 132.63, 127.93, 117.30, 111.52, 74.32, 73.59, 34.47, 31.88, 29.97, 29.36, 29.17, 25.12, 22.84, 18.18, 14.29, 12.94. TOF MS-ES$^+$, calculated mass: C$_{46}$H$_{76}$O$_9$Si$_2$ [M+Na]=851.4926, measured mass: [M+Na]=851.4966.

Series of Triethylsilyl Resveratrol Derivatives with Acyl Groups.

3,5-O-triethylsilyl resveratrol (9) (1 eq.) was dissolved in tert-butanol, and the vinyl ester of the corresponding fatty acid (6 eq.) and Novozyme 435® (approx. 100 mg) were added. The reaction was allowed to progress for 60 h at 50° C. under orbital shaking. After this period, the reaction was filtered in order to remove the enzyme and washed with a little methanol. The obtained crude was purified by means of silica gel column chromatography with a gradient using a mixture of hexane and ethyl acetate as the mobile phase (100:0-1:1).

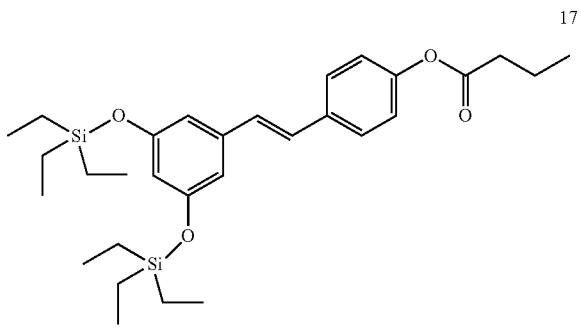 [SMILES: CCCC(=O)Oc1ccc(/C=C/c2cc(O[Si](CC)(CC)CC)cc(O[Si](CC)(CC)CC)c2)cc1]

3,5-O-triethylsilyl-4'-butanoyl resveratrol, compound 17. Yield=39.0%. $R_f$=0.29 (hexane:ethyl acetate—8:1). RMN of $^1$H (400 MHz, CDCl$_3$): δ=7.37 (d, J=8.0 Hz, 2H), 6.93 (d, J=16.2 Hz, 1H), 6.87-6.76 (m, 3H), 6.60 (d, J=2.2 Hz, 2H), 6.27 (t, J=2.1 Hz, 1H), 2.34 (t, 2H), 1.66 (m, 2H), 1.00 (t, J=7.9 Hz, 18H), 0.94 (t, 3H), 0.74 (q, J=7.9 Hz, 12H). RMN of $^{13}$C (101 MHz, CDCl$_3$): δ=179.26 (CO), 156.55 (2×Cq), 155.32 (Cq), 139.40 (Cq), 130.14 (Cq), 128.25 (CH arom), 127.91 (2×CH arom), 126.56 (CH arom), 115.57 (2×CH arom), 111.38 (2×CH arom), 110.91 (CH arom), 29.65 (CH$_2$CO), 22.66 (CH$_2$CH$_3$), 14.06 (CH$_3$), 6.60 (6×CH$_2$Si), 4.99 (6×CH$_3$CH$_2$Si).

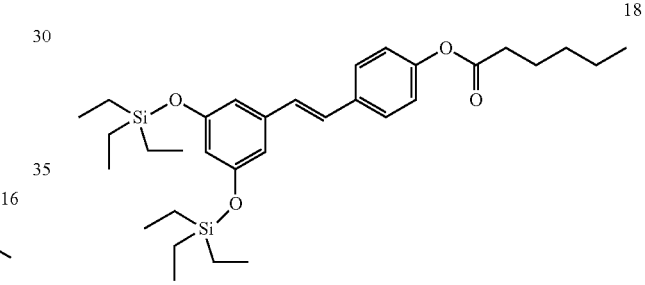

3,5-O-triethylsilyl-4'-hexanoyl resveratrol, compound 18. Yield=66.0%. $R_f$=0.29 (hexane:ethyl acetate—8:1). RMN of $^1$H (400 MHz, CDCl$_3$): δ=7.36 (d, J=8.0 Hz, 2H), 6.93 (d, J=16.2 Hz, 1H), 6.85-6.76 (m, 3H), 6.59 (d, J=2.2 Hz, 2H), 6.26 (t, J=2.2 Hz, 1H), 2.33 (t, J=7.5 Hz, 2H), 1.70-1.56 (m, 2H), 1.32 (m, 2H), 1.00 (t, J=7.9 Hz, 18H), 0.92-0.84 (m, 3H), 0.79-0.69 (m, 12H). RMN of $^{13}$C (101 MHz, CDCl$_3$): δ=180.26 (CO), 156.54 (2×Cq), 155.39 (Cq), 139.41 (Cq), 130.07 (Cq), 128.28 (CH arom), 127.88 (2×CH arom), 126.49 (CH arom), 115.57 (2×CH arom), 111.36 (2×CH arom), 110.88 (CH arom), 34.02 (CH$_2$CO), 31.16 (CH$_2$CH$_2$), 24.33 (CH$_2$CH$_2$), 22.24 (CH$_2$CH$_3$), 13.80 (CH$_3$), 6.58 (6×CH$_2$Si), 4.98 (6×CH$_3$CH$_2$Si).

3,5-O-triethylsilyl-4'-propanoyl resveratrol, compound 16. Yield=34.0%. $R_f$=0.35 (hexane:ethyl acetate—8:1). RMN of $^1$H (400 MHz, CDCl$_3$): δ=7.37 (d, J=8.3 Hz, 2H), 6.94 (d, J=16.2 Hz, 1H), 6.87-6.73 (m, 3H), 6.60 (d, J=2.3 Hz, 2H), 6.28 (t, J=2.1 Hz, 1H), 2.33 (q, 2H), 1.66 (t, 3H), 1.01 (t, J=7.9 Hz, 18H), 0.75 (q, J=7.9 Hz, 12H). RMN of $^{13}$C (101 MHz, CDCl$_3$): δ=180.10 (CO), 156.55 (2×Cq), 155.26 (Cq), 139.39 (Cq), 130.20 (Cq), 128.24 (CH arom), 127.91 (2×CH arom), 126.60 (CH arom), 115.56 (2×CH arom), 111.38 (2×CH arom), 110.93 (CH arom), 29.67 (CH$_2$CO), 14.06 (CH$_3$CH$_2$CO), 6.60 (6×CH$_2$Si), 5.00 (6×CH$_3$CH$_2$Si).

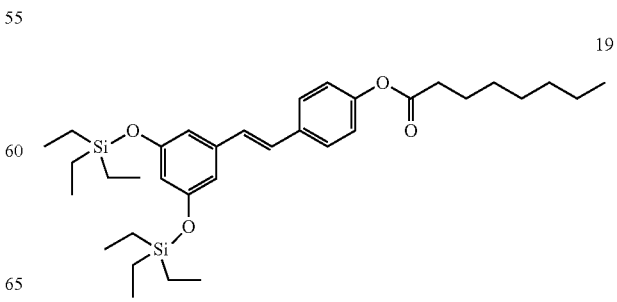

3,5-O-triethylsilyl-4'-octanoyl resveratrol, compound 19. Yield=63.0%. $R_f$=0.25 (hexane:ethyl acetate—8:1). RMN of $^1$H (400 MHz, CDCl$_3$): δ=7.36 (d, J=8.3 Hz, 2H), 6.93 (d, J=16.3 Hz, 1H), 6.87-6.72 (m, 3H), 6.59 (d, J=2.2 Hz, 2H), 6.26 (t, J=2.2 Hz, 1H), 2.33 (t, J=7.5 Hz, 2H), 1.62 (q, J=7.4 Hz, 2H), 1.29 (m, 8H), 1.00 (t, J=7.9 Hz, 18H), 0.86 (t, J=6.6 Hz, 3H), 0.74 (q, J=7.9 Hz, 12H). RMN of $^{13}$C (101 MHz, CDCl$_3$): δ=180.38 (CO), 156.54 (2×Cq), 155.43 (Cq), 139.40 (Cq), 130.04 (Cq), 128.27 (CH arom), 127.87 (2×CH arom), 126.48 (CH arom), 115.56 (2×CH arom), 111.34 (2×CH arom), 110.87 (CH arom), 34.07 (CH$_2$CO), 31.58 (CH$_2$CH$_2$), 28.97 (CH$_2$CH$_2$), 28.85 (CH$_2$CH$_2$), 24.64 (CH$_2$CH$_2$), 22.54 (CH$_2$CH$_3$), 13.98 (CH$_3$), 6.58 (6×CH$_2$Si), 4.98 (6×CH$_3$CH$_2$Si).

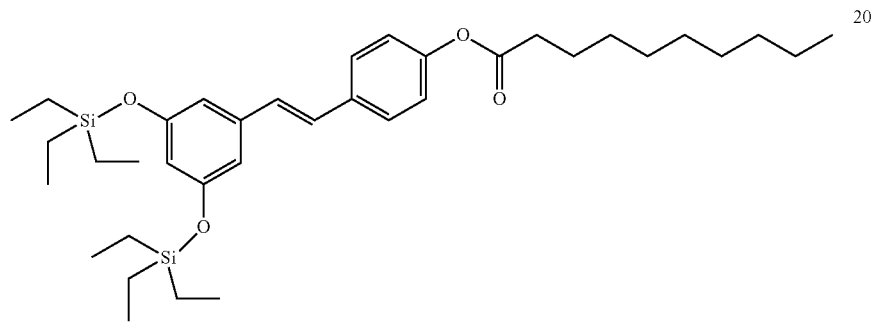 [SMILES: CCCCCCCCCC(=O)Oc1ccc(/C=C/c2cc(O[Si](CC)(CC)CC)cc(O[Si](CC)(CC)CC)c2)cc1]

3,5-O-triethylsilyl-4'-decanoate resveratrol, compound 20. Yield=89.0%. $R_f$=0.25 (hexane:ethyl acetate—8:1). RMN of $^1$H (400 MHz, CDCl$_3$): δ=7.36 (d, J=8.2 Hz, 2H), 6.93 (d, J=16.2 Hz, 1H), 6.88-6.74 (m, 3H), 6.59 (d, J=2.2 Hz, 2H), 6.26 (t, J=2.2 Hz, 1H), 2.33 (t, J=7.5 Hz, 2H), 1.62 (q, J=7.4 Hz, 2H), 1.41-1.18 (m, 12H), 1.00 (t, J=7.9 Hz, 18H), 0.86 (t, J=6.8 Hz, 3H), 0.74 (q, J=7.8 Hz, 12H). RMN of $^{13}$C (101 MHz, CDCl$_3$): δ=180.43 (CO), 156.54 (2×Cq), 155.48 (Cq), 139.42 (Cq), 130.00 (Cq), 128.30 (CH arom), 127.86 (2×CH arom), 126.44 (CH arom), 115.57 (2×CH arom), 111.34 (2×CH arom), 110.86 (CH arom), 34.08 (CH$_2$CO), 31.82 (CH$_2$CH$_2$), 29.35 (CH$_2$CH$_2$), 29.21 (CH$_2$CH$_2$), 29.20 (CH$_2$CH$_2$), 29.02 (CH$_2$CH$_2$), 24.64 (CH$_2$CH$_2$), 22.62 (CH$_2$CH$_3$), 14.02 (CH$_3$), 6.57 (6×CH$_2$Si), 4.98 (6×CH$_3$CH$_2$Si).

Example 2: Viability and Neuroprotection Assays

The SH-SY5Y neuroblastoma cell line was cultured in petri dishes pre-treated with collagen (100 ng/ml) with F12 medium supplemented with penicillin/streptomycin and 10% inactivated fetal bovine serum.

Cell viability assays with neurons were prepared in 96-well plates pre-treated with collagen by seeding 20,000 cells/well in a volume of 100 μL and incubating the cells for 24 h before the addition of the compounds. The compounds to be tested were dissolved in DMSO and added in three different concentrations (1, 10, and 100 μM) in order to determine their toxicity. The final percentage of DMSO in each well was adjusted to 1%. The cell viability was evaluated 24 h after the addition of the compounds by means of the MTT assay according to the manufacturer's method. Mean values and standard deviations were calculated from at least eight different measurements from several independent experiments.

For the neuroprotection assay, the neurons were cultured and seeded in the same manner as for the cell viability assay. The compounds to be tested were dissolved in DMSO and added in three different concentrations (1, 10, and 100 μM) and, after 10-minute incubation, hydrogen peroxide (100 μM) was added to the medium. The final percentage of DMSO in each well was adjusted to 1%. The cell viability was evaluated 24 h after the addition of the compounds by means of the MTT assay according to the manufacturer's method. Mean values and standard deviations were calculated from at least eight different measurements from several independent experiments. Neuronal recovery was calculated by normalizing the results of the neuronal viability experiments after the addition of the compounds of the invention and H$_2$O$_2$ to the positive control of each experiment (neurons+H$_2$O$_2$).

It is observed that the RES 10 μM control recovers up to 50% of cell viability (FIGS. 1 to 5, indicated by the broken line). In contrast, many of the silylated derivatives of the invention recover between 80 and 120% viability at concentrations between 1 and 100 μM. Some appear to exhibit toxicity at 100 μM.

Example 3: Inflammation Assay

RAW 264.7 macrophages were cultured in P75 with high-glucose DMEM supplemented with penicillin/streptomycin and 10% inactivated fetal bovine serum.

The cell viability assays with RAW macrophages were prepared in 96-well plates by seeding 25,000 cells/well in a volume of 100 μL and incubating the cells for 4 h before the addition of the compounds. The compounds to be tested were dissolved in DMSO and added in three different concentrations (1, 10, and 100 μM) in order to determine their toxicity. The final percentage of DMSO in each well was adjusted to 1%. The cell viability was evaluated 24 h after the addition of the compounds by means of the MTT assay according to the manufacturer's method. Mean values and standard deviations were calculated from at least eight different measurements from several independent experiments.

For the testing of mitigation of damage caused by the addition of LPS, the RAW 264.7 macrophages were cultured according to the procedure described above. The compounds to be tested were dissolved in DMSO and added in three different concentrations (1, 10, and 100 μM) and, after 10-minute incubation, LPS (100 ng/ml) was added to the medium. The final percentage of DMSO in each well was adjusted to 1%. The cell viability was evaluated 24 h after the addition of the compounds by means of the MTT assay according to the manufacturer's method. Mean values and standard deviations were calculated from at least eight different measurements from several independent experiments.

In this assay, it is observed that the 10 µM resveratrol control recovers up to 62% of cell viability (FIGS. 6 to 10, indicated by the broken line). In contrast, several of the silylated derivatives of the invention recover greater cell viability at concentrations between 1 and 100 µM. Some appear to exhibit toxicity at 100 µM.

Example 4: Measurements of Inflammation Parameters in Assay with LPS

To determine the production of cytokines, $5 \times 10^5$ RAW 264.7 macrophages were seeded in 24-well plates (0.5 ml per well). The compounds to be tested were then added (10 µM), and the macrophages were either stimulated or not through the addition of LPS (1 µg/ml) to the culture medium. After 24 hours, the levels of IL-6 and TNF-α were measured in the supernatants by ELISA using the capture and biotinylated antibodies from BD PharMingen and PrepoTech following known protocols. The levels of NO in the supernatants at 24 hours were measured indirectly by determining the nitrite concentration in the medium using the Griess reagent according to established protocol. A minimum of two independent experiments and three replicates per experiment were performed for each measured value. The values are expressed as the mean±standard deviation.

In the previous assay, the levels of various inflammation parameters were measured (TNF-α, NO, and IL-6) by ELISA after treatment with RES or with some of the compounds of the invention (2, 3, 5, 6, 8, and 9).

Figure 11:
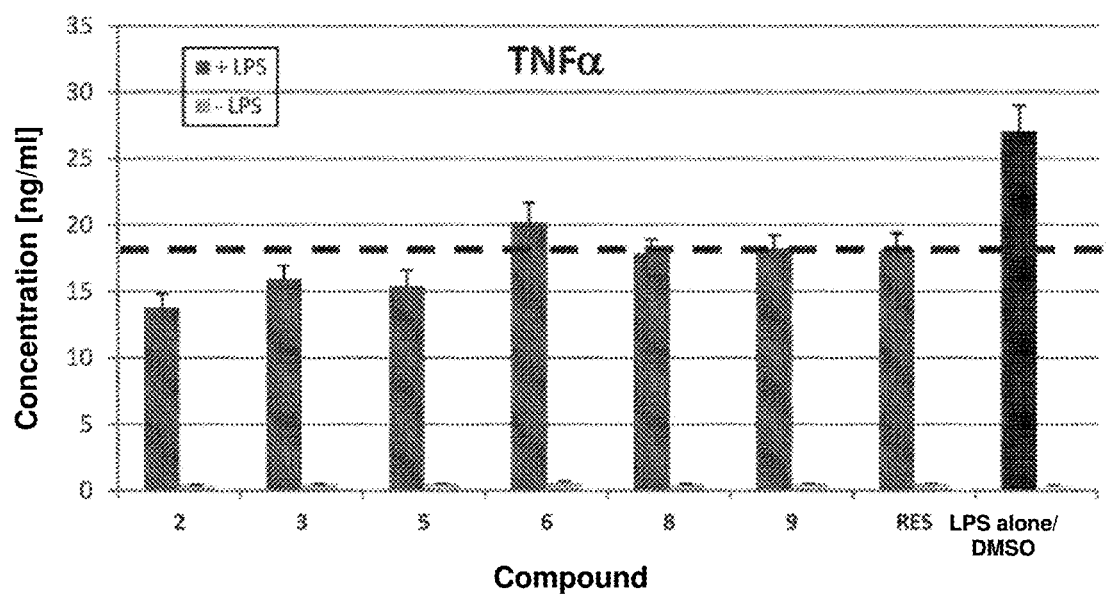
FIG. 11. Concentration of TNF-alpha in culture medium after inflammation by LPS in RAW macrophages and treatment with the different compounds 2-9.
Figure 12:
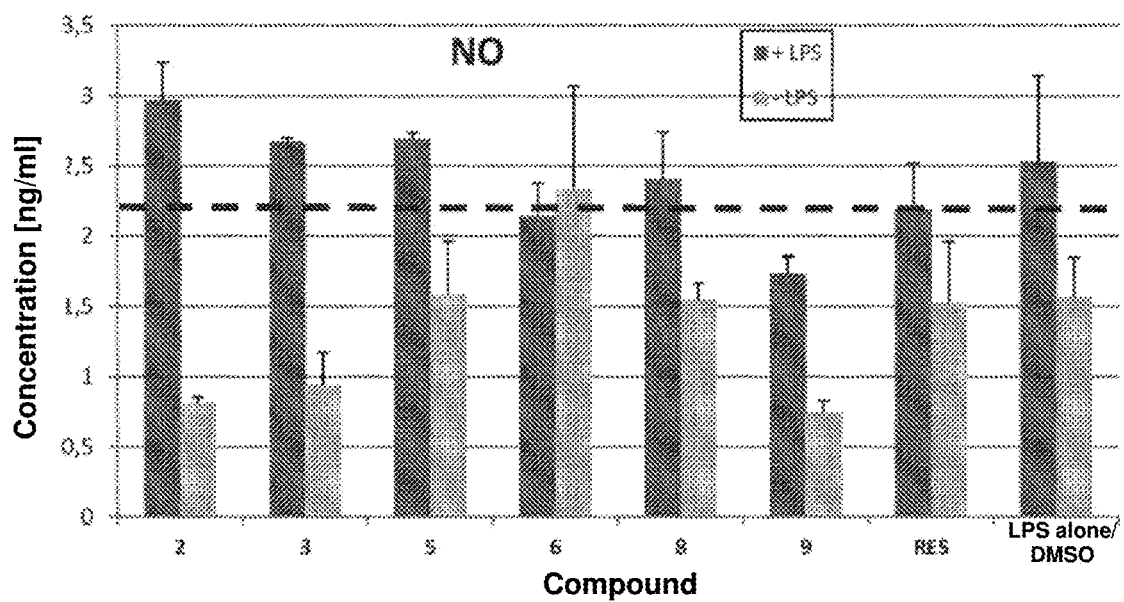
FIG. 12. Concentration of NO in culture medium after inflammation by LPS in RAW macrophages and treatment with the different compounds 2-9.
Figure 13:
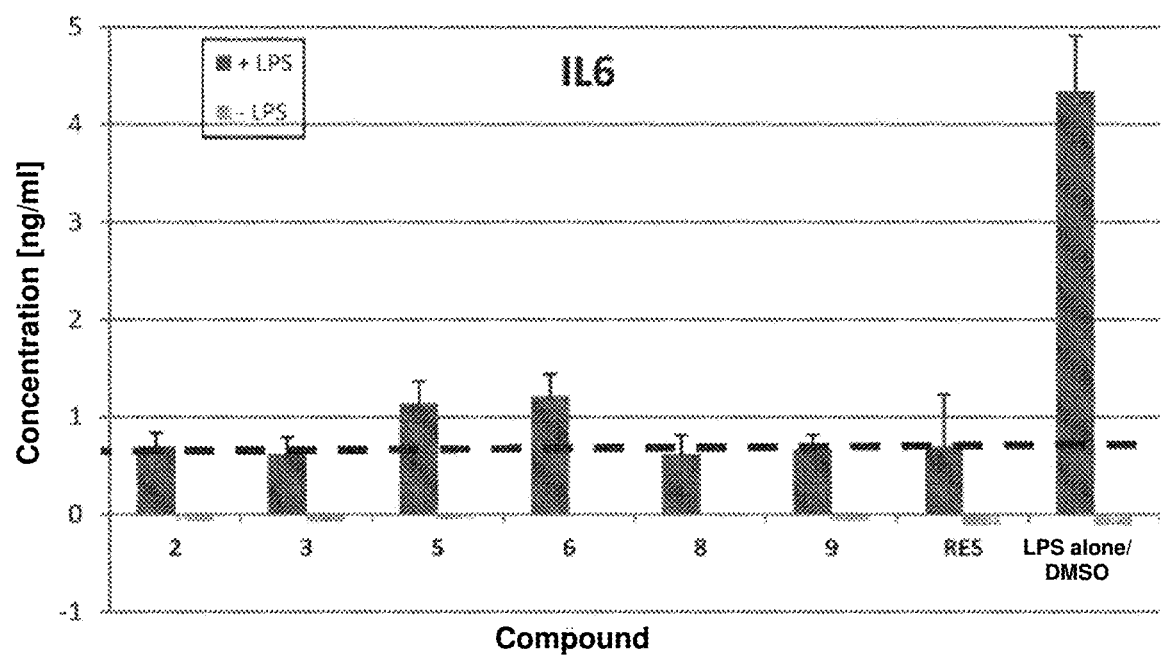
FIG. 13. Concentration of IL6 in culture medium after inflammation by LPS in RAW macrophages and treatment with the different compounds 2-9.

It is observed that the control of RES 10 µM significantly decreases inflammatory parameters (TNF-α, NO, and IL-6) (FIGS. 11, 12, and 13, respectively, indicated by the bar in bold). In contrast, several of the silylated derivatives of the invention improve RES and decrease these parameters even further.

Example 5: Evaluation of the Neuroprotective Capacity of Various Silylated Compounds in a Model of Neurodecqeneration in Zebrafish Larvae Induced by Pentylenetetrazole (PTZ)

The objective of this assay was to analyze the protective effect of various derivatives of resveratrol in a model of neurotoxicity induced by the neurotoxin pentylenetetrazole (PTZ). As an experimental model, the zebrafish (*Danio rerio*) was used to study the effect of the compounds on acetylcholinesterase activity (AChE) in larvae at 5 days post-fertilization (dpf).

Studies of the central nervous system (CNS) in zebrafish show that, at 24 hours of development, the brain of the embryo has already segmented and already has some structures such as the neural tube, the notochord, and the somites (muscle, and bone precursors). At 5 days post-fertilization (5 dpf), the animal has formed sensory organs such as eyes and otoliths. In addition, the heart, liver, kidneys, and pancreas, as well as the circulatory, digestive, and nervous systems, are fully functional. At this time, the animal is able to respond to visual, olfactory, and mechanical stimuli and begins the search for food.

Zebrafish embryos were seeded in 50 ml of dilution water (AD) in a Petri dish and grown to 5 dpf (larval stage). Only those larvae that did not exhibit any type of external anomaly were used to perform the assay. Next, the larvae were transferred using a Pasteur pipette to a 24-well microplate, so that each well contained five larvae, making ten replicates per condition. First, the pre-treatment of the 5 dpf larvae was performed. For this, the larvae were incubated at 26±1° C. for 1 hour in a volume of 2 ml of AD for the two control groups (Control and Control+PTZ), of physostigmine (Phys) 20 µM, which is a commercial inhibitor of the enzyme AChE for the Phys group, and of the test compounds at a concentration of 10 µM. A medium exchange was then carried out, and the larvae were incubated with the compounds in combination with 5 mM PTZ for 6 hours at 26±1° C. After this incubation period, all of the larvae were examined, and it was determined that the general state of the larvae was totally normal, without any visible anomaly or anomalous behavior. Finally, the larvae were processed for the analysis of the AChE activity.

In order to determine the AChE levels, larvae processing was carried out according to the established technical study protocol once the experimental period was completed. The larvae were homogenized mechanically, and the samples were centrifuged to obtain the supernatant, which were used to determine the levels of the AChE enzyme as a function of the treatments administered. In addition, the determination of total protein of each experimental group was carried out according to the established technical study protocol. Finally, the AChE levels determined in the control group were taken as a reference measurement and deemed to be 100%.

Figure 14:
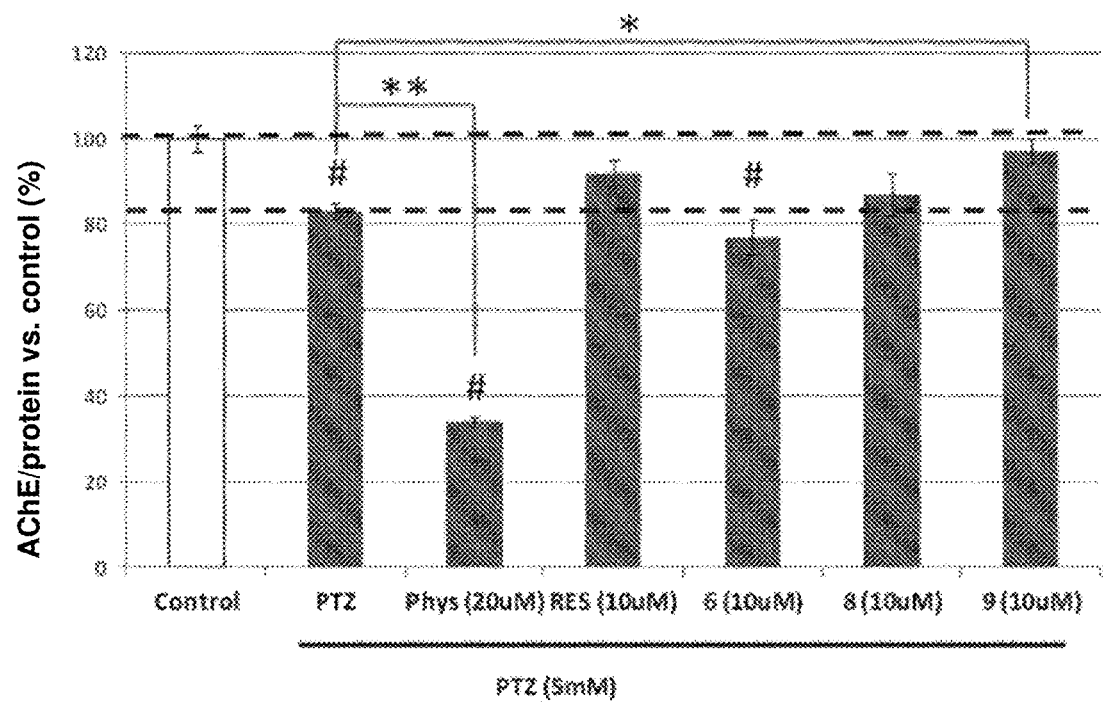
FIG. 14. AChE activity regarding the control of the compounds RES, 6, 8, and 9. An ANOVA statistical test was carried out, followed by Dunnett's multiple comparison test. It is considered significant when #P<0.05 relative to the control; *P<0.05, **P<0.01 relative to the control+PTZ.
Figure 15:
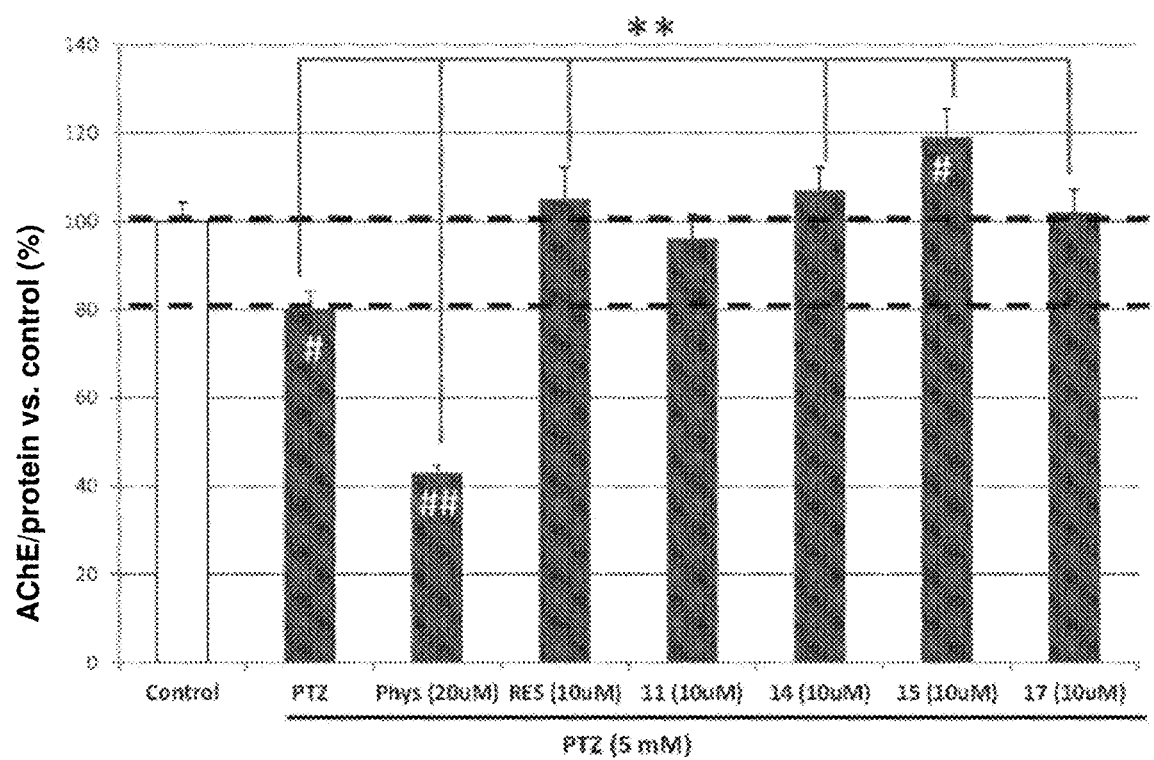
FIG. 15. AChE activity regarding the control of the compounds RES, 11, 14, 15, and 17. An ANOVA statistical test was carried out, followed by Dunnett's multiple comparison test. It is considered significant when #P<0.05 relative to the control; *P<0.05, **P<0.01 relative to the control+PTZ.

The results of this assay showed that silylated derivatives 9 (3,5-dithyrylsilyl resveratrol) and 15 (3,5-O-ditriisopropylsilyl-4'-(6-octanaoyl)glucosyl resveratrol) significantly prevent the decrease in AChE activity induced by PTZ in 5 dpf larvae, exhibiting a clear neuroprotective effect (see FIGS. 14 and 15). Silylated derivatives 8, 14, and 17 show a lower neuroprotective effect similar to that observed for resveratrol (RES).

Example 6: Testing of Compound 15 in Animal Model of Huntington's Disease

Compound 15 was investigated as a possible treatment in a mouse model of Huntington's disease. The compound resveratrol (RES) was added as a reference.

In this model, increasing amounts of 3-nitro-propionic acid (3NP) are injected into the mice, causing lesions with a phenotype very similar to that of Huntington's disease, both mechanically and pathologically. Once the damage was caused, the mice were treated with RES, compound 15, or vehicle, and we studied the effect thereof on the mouse on the basis of different parameters. Behavioral studies (rotarod test), an assessment was made of motor capacity (tabulated on a scale of 0 normal to 4 incapable, in several parameters such as general mouse dystonia, ability to flip over, and the ability to explore), weight was monitored, and subsequent measurements were taken such as of the inhibition of pro-inflammatory cytokines in plasma or brain.

Figure 16:
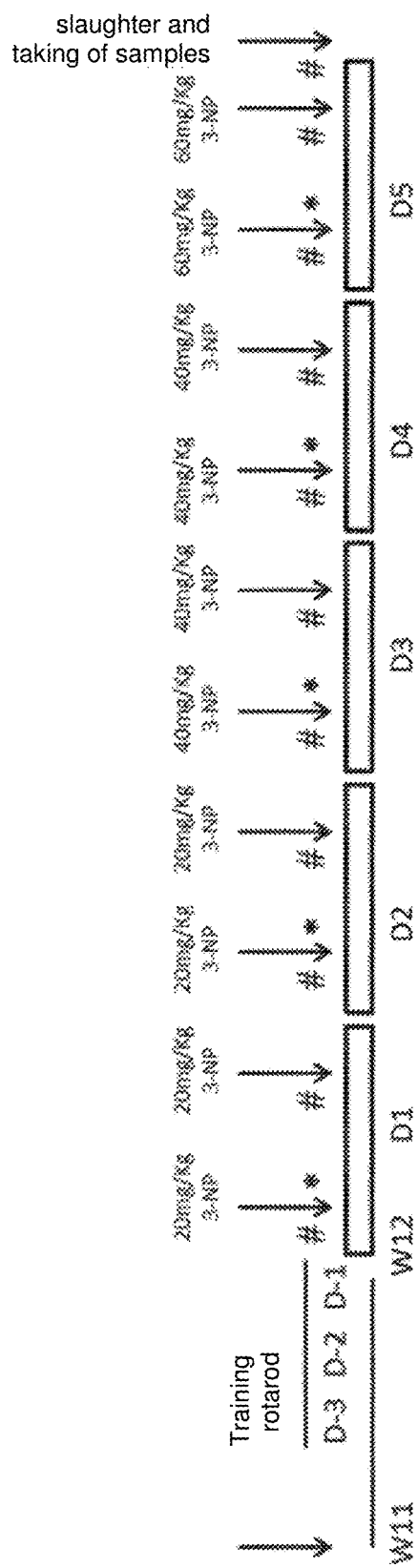
FIG. 16: Schematic of the design of the experiment conducted in example 6.
Figure 17A:
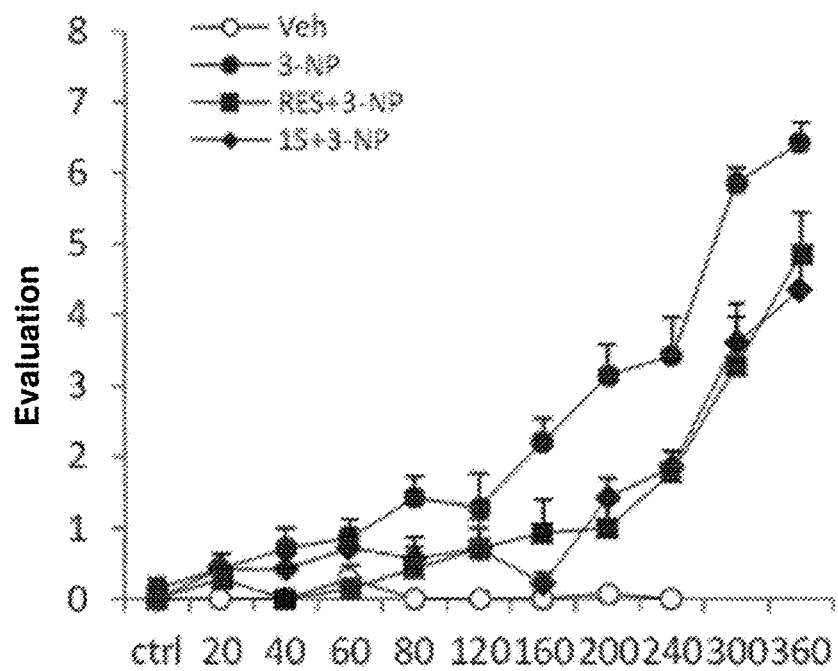
FIG. 17: a) Evaluation of the motor capacity (sum of four movement parameters) of the groups of mice treated with the compounds RES and 15; b) Time (in seconds) in the rotarod of the groups of mice treated with the compounds RES and 15 on day 5; c) Average weight of the groups of mice treated with the compounds RES and 15 on day 5; d) Amount of interleukin IL-6 in plasma of the groups of mice treated with the compounds RES and 15.
Figure 17B:
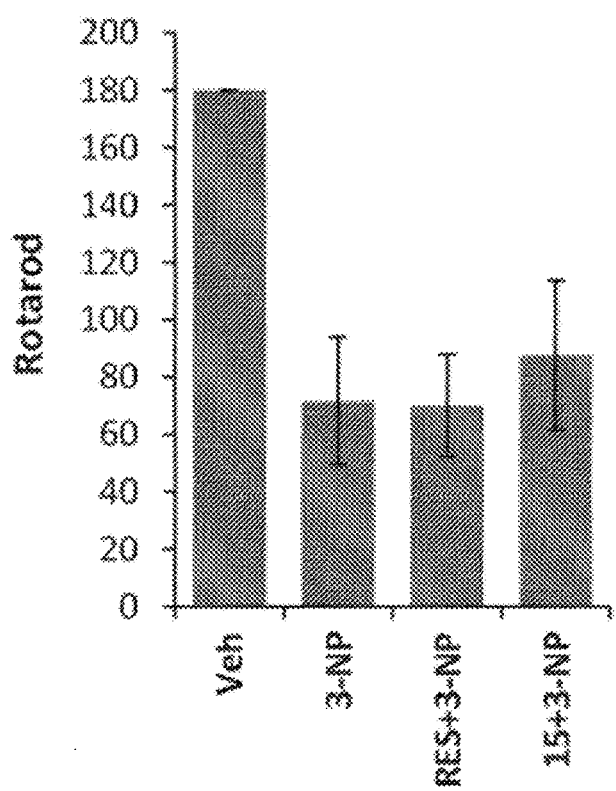
Figure 17C:
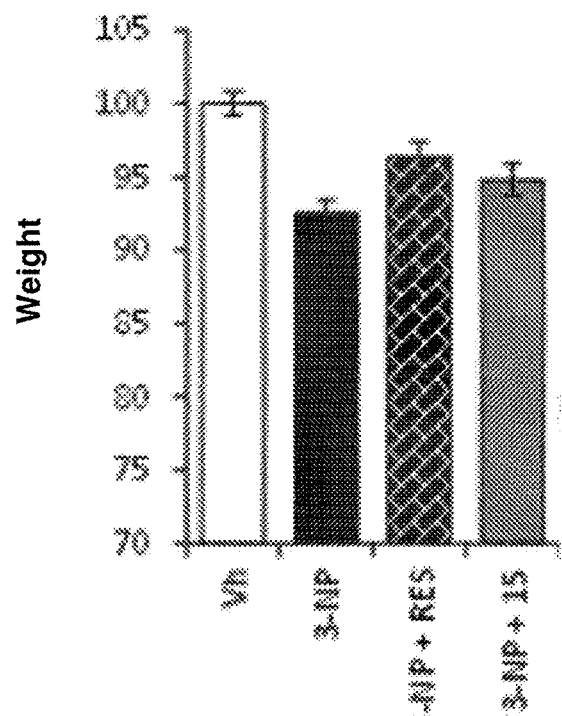
Figure 17D:
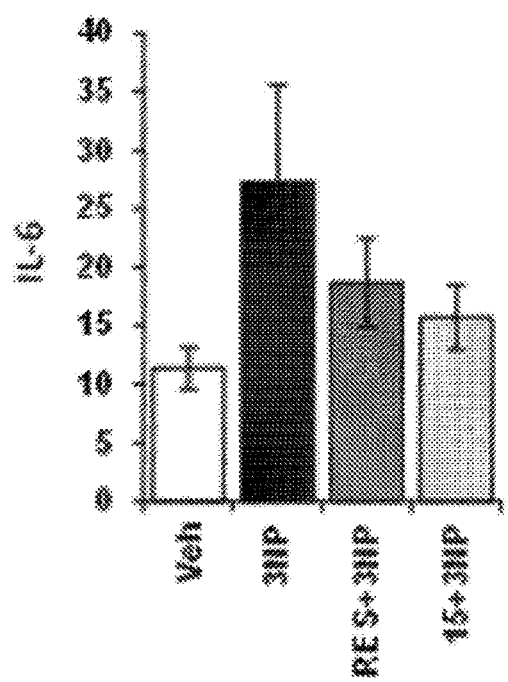

The design of the experiment is shown in FIG. 16. #=Behavioral study and rotarod test; φ Administration of the compound; W=weeks of age of the mice; D=Day of the experiment.

The results are shown in FIG. 17. In all cases, it is observed how compound 15 is capable of improving the phenotype caused by 3NP either by decreasing the severity of the motor lesions or the levels of pro-inflammatory cytokines such as IL-6, or by increasing the weight of the animals. The differences between compound 15 and RES are not great, probably because this animal model is short and very aggressive. It would be advisable to test compound 15 in a model in which the neuronal, motor, and inflammatory damage was slower and more progressive, because it would be closer to the reality of the patient and because the treatment is perhaps much more efficient in a more progressive model.

Example 7: Testing of Compound 15 in Animal Model of Multiple Sclerosis

Compound 15 was investigated as a possible treatment in a mouse model of multiple sclerosis. The compound resveratrol (RES) was added as a reference. An experimental allergic encephalomyelitis model, EAE, was used as an animal model of multiple sclerosis.

In this model, mice are injected with myelin oligodendrocyte glycoprotein (MOG, $MOG_{35-55}$, is the 21 amino acid peptide corresponding to the sequence from positions 35 to 55 of the MOG glycoprotein) and virus pertussis (pertussis toxin, PTX) in order to induce the disease. Two days after induction, a new dose of the virus was given again, because some mice were not developing symptoms of EAE. Once the damage was caused, the mice were treated with RES, compound 15, or vehicle, and we studied the effect thereof on the mouse on the basis of different motor parameters on a scale from 0 normal to 4 incapable.

The design of the experiment is shown below:
Experimental Groups:
  Vehicle without tween-80 emulsifier (control EAE without T)
  Vehicle with tween-80 emulsifier (EAE-T control)
  Preventive RES (without tween-80 emulsifier) (RES-PREV)
  Therapeutic RES (no tween-80 emulsifier) (RES-TERAP)
  Preventive compound 15 (with tween-80 emulsifier) (compound 15-PREV)
  Therapeutic compound 15 (with tween-80 emulsifier) (compound 15-TERAP)
  Preventive Regimen (Pretreatment. PREV):

The (intraperitoneal) administration of the compounds (resveratrol, compound 15, and vehicle, with or without tween-80) is started 5 days after induction. 250 µL of the compound in question (20 mg/kg) were injected twice a week and the treatment was maintained for 3 weeks. The treatment was then stopped, but the state of the mice was monitored for another 3 weeks (47 days total).

Therapeutic Regimen (Therapeutic. TERAP):
The (intraperitoneal) administration of the compounds (resveratrol, compound 15, and vehicle, with or without tween-80) is started 12 days after induction. 250 µL of the compound in question (20 mg/kg) were injected twice a week and the treatment was maintained for 2 weeks. The treatment was then stopped, but the state of the mice was monitored for another 3 weeks (47 days total).

Figure 18A:
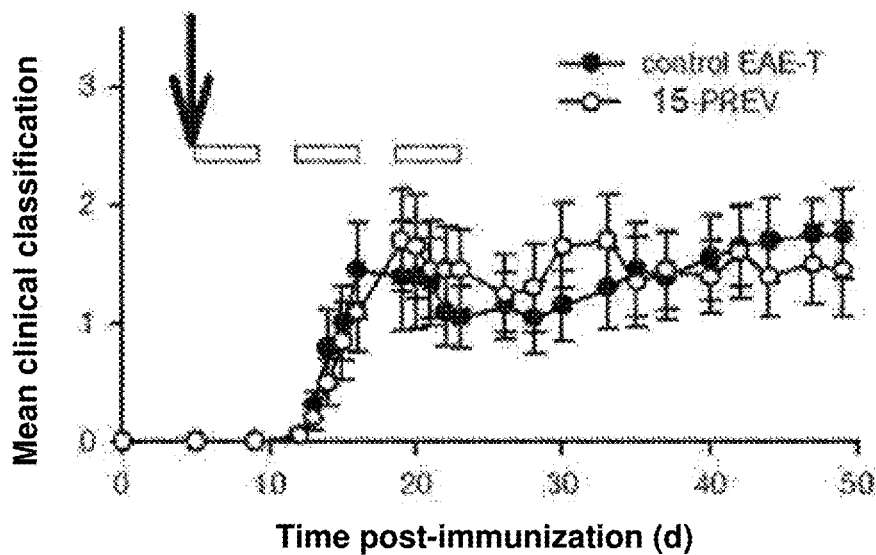
FIG. 18: a) Evaluation of the motor capacity of the groups of mice treated preventively with compound 15 and the EAE-T control; b) Evaluation of the motor capacity of the groups of mice treated preventively with the compound RES and the EAE control without T; c) Evaluation of the motor capacity of the groups of mice treated therapeutically with compound 15 and the EAE-T control; d) Evaluation of the motor capacity of the groups of mice treated therapeutically with the RES compound and the EAE control without T.
Figure 18B:
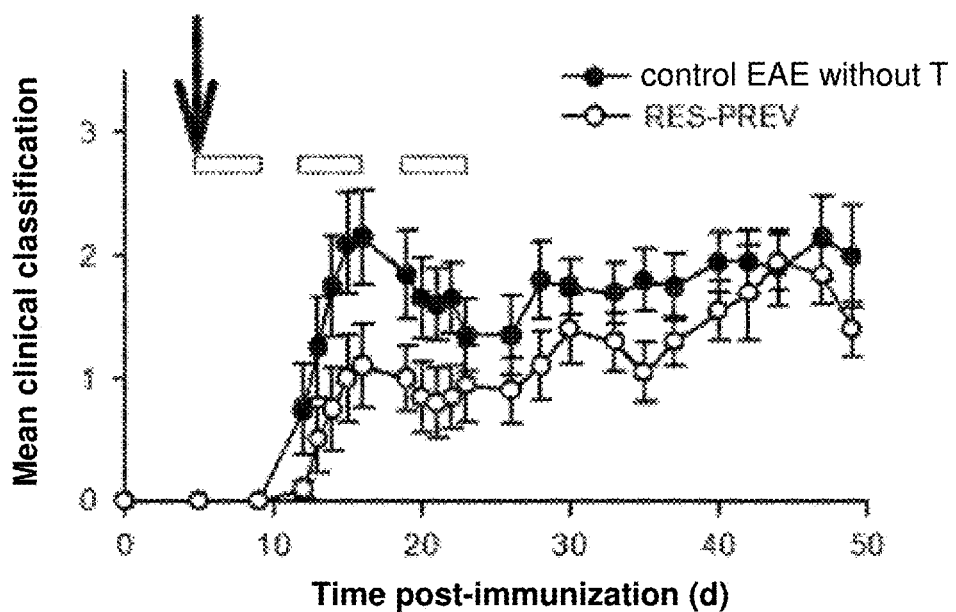

When performing a preventive treatment (see FIGS. 18*a* and 18*b*), it is observed that compound 15 does not have a great effect on motor capacity (a). On the other hand, RES does reduce damage on a motor level with this preventive treatment (b).

Figure 18C:
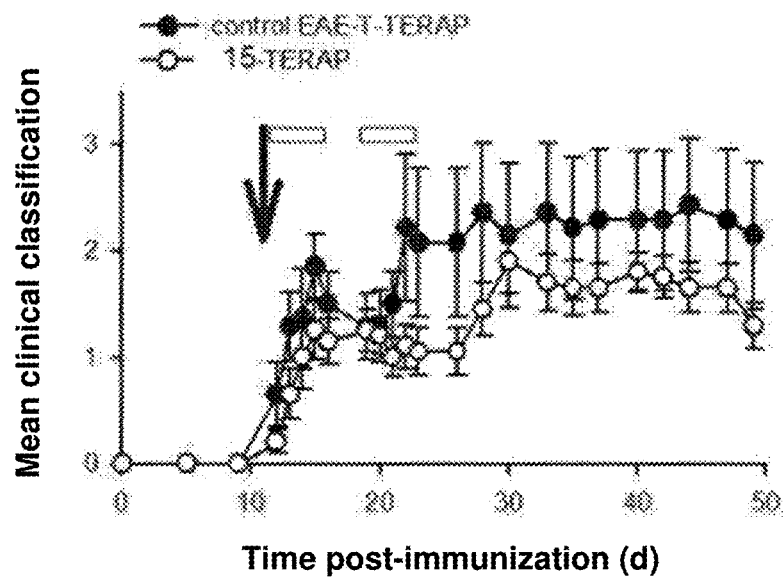
Figure 18D:
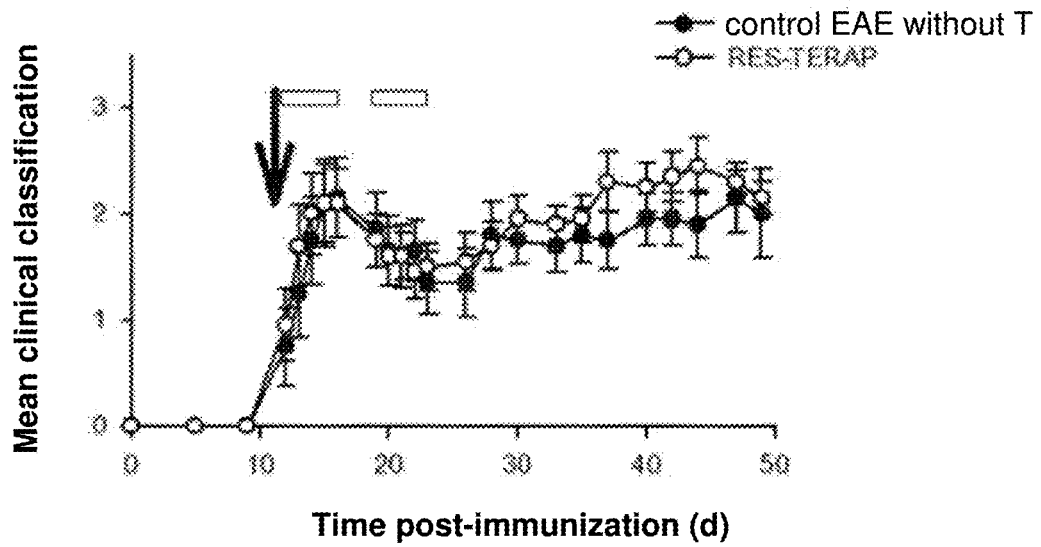

When performing a therapeutic treatment (see FIGS. 18*c* and 18*d*), it is observed that compound 15 improves the clinical classification of the motor capacity of the mice compared to the control, especially between days 20-30 of the test (second week of administration of the compound). It is also striking that this improvement in the clinical classification was maintained during days 30-47, when the administration of the drug had already been interrupted. In contrast, the mice do not appear to improve in terms of the damage produced when RES is administered in therapeutic mode.

It should also be highlighted that the tween-80 emulsifier appears to have a pharmacological effect per se (see controls of the preventive treatment groups, a vs. b), which would be masking, at least partially, the possible effect of compound 15 in reducing the damage in the multiple sclerosis model.

It is important to note that 20 mg/kg of each compound (RES and compound 15) was administered, but given the large differences in molecular weight of the two compounds (MW compound 15=3×MW RES), the administered doses are not comparable. Thus, the dose administered (in µmol/kg) of RES≅3× dose of compound 15, so that although the two compounds show a similar efficacy in the treatment of EAE, compound 15 does so at a much lower concentration than RES and is therefore much more effective.

What is claimed is:
1. A compound of formula (I'):

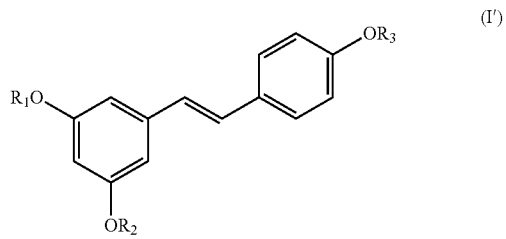

wherein $R_1$, $R_2$, and $R_3$ are independently selected from the group consisting of H, a $SiR_4R_5R_6$ group, —NH(CO)$R_7$ group, and a carbohydrate, and
wherein $R_4$, $R_5$, and $R_6$ are independently selected from the group consisting of linear $C_1$-$C_6$ alkyl, branched $C_1$-$C_6$ alkyl and a phenyl group and $R_7$ is selected from the group consisting of a linear $C_1$-$C_{12}$ alkyl and branched C1-$C_{12}$ alkyl, with the proviso that at least one of $R_1$, $R_2$, and $R_3$ is a $SiR_4R_5R_6$ group and that it is not one of the following compounds:
  (E)-(5-(4-(trimethylsilyloxy)styryl)-1,3-phenylene)bis(oxy)bis(trimethylsilane),
  (E)-4-(3,5-bis(triisopropylsilyloxy)styryl)phenol,
  (E)-3-(tert-butyldimethylsilyloxy)-5-(4-(tert-butyldimethylsilyloxy)styryl)phenol,
  (E)-4-(3,5-bis(tert-butyldimethylsilyloxy)styryl)phenol,
  (E)-3-(tert-butyldimethylsilyloxy)-5-(4-hydroxystyryl)phenol,
  (E)-5-(4-(tert-butyldimethylsilyloxy)styryl)benzene-1,3-diol,
  (E)-(5-(4-(tert-butyldimethylsilyloxy)styryl)-1,3-phenylene)bis(oxy)bis(tert-butyldimethylsilane),
wherein $R_1$ and $R_2$ are a $SiR_4R_5R_6$ group and $R_3$ is selected from the group consisting of H, —NH(CO)$R_7$, and the following carbohydrate:

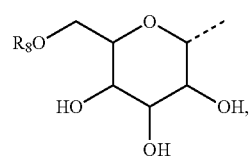

and wherein $R_8$ is selected from the group consisting of H, and —C(O)—$R_9$, and $R_9$ is selected from the group consisting of a $C_1$-$C_{22}$ alkyl and a $C_1$-$C_{22}$ alkenyl, or wherein $R_1$ and $R_3$ are a $SiR_4R_5R_6$ group and $R_2$ is selected from the group consisting of H, —NH(CO)$R_7$, and the following carbohydrate:

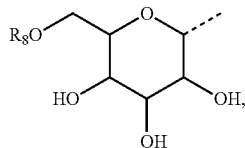

and wherein $R_8$ is selected from the group consisting of H, and —C(O)—$R_9$, and $R_9$ is selected from the group consisting of a $C_1$-$C_{22}$ alkyl and a $C_1$-$C_{22}$ alkenyl, or
  wherein $R_1$, $R_2$, and $R_3$ are a $SiR_4R_5R_6$ group, or
  wherein the compound is selected from the following group consisting of:

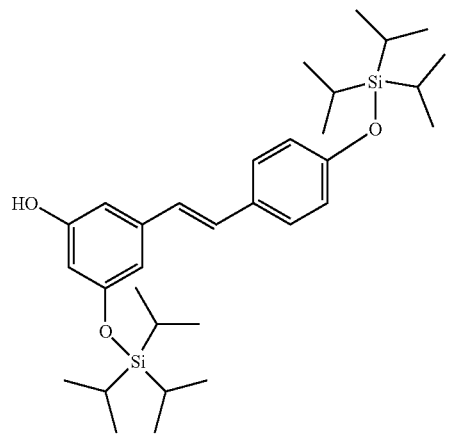

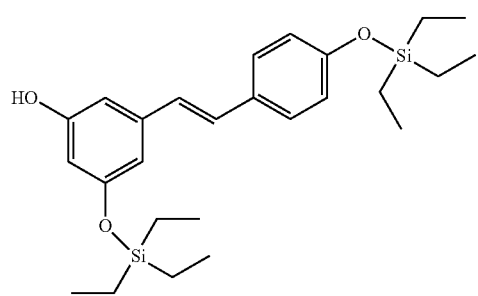

or the compound is selected from the following group consisting of:

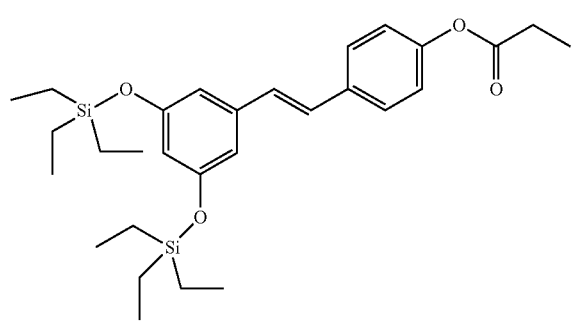

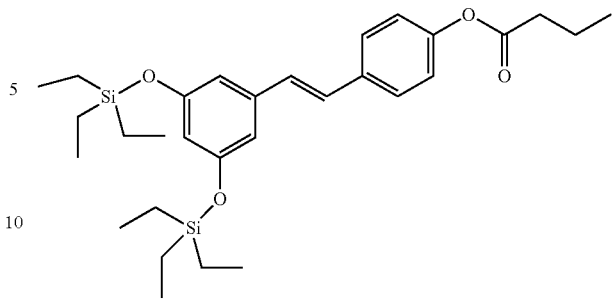

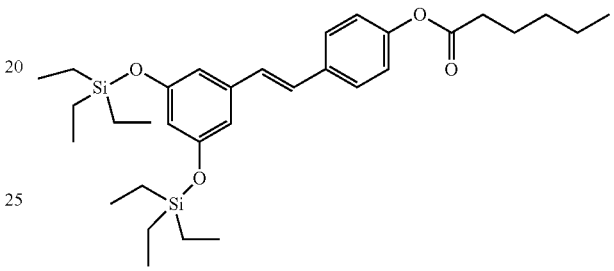

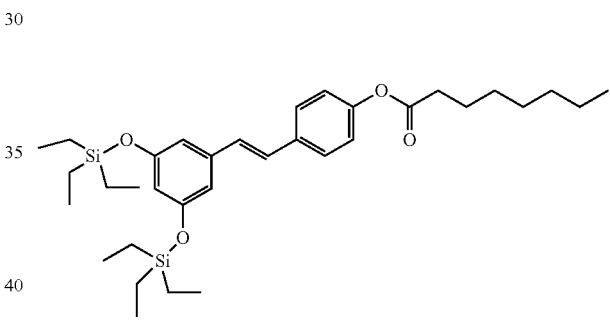

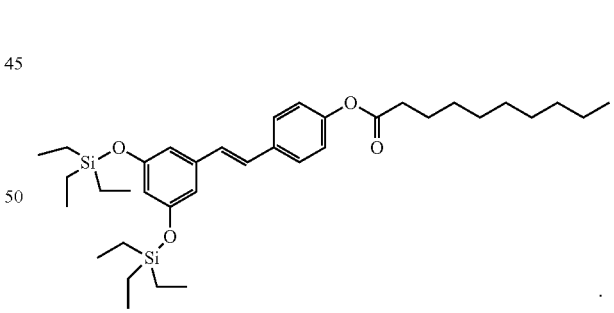

2. The compound of claim 1, wherein $R_4$ and $R_5$ are selected from the group consisting of methyl, ethyl, and isopropyl and $R_6$ is selected from the group consisting of tert-butyl, ethyl, and isopropyl.

3. The compound of formula (I') according to claim 1, wherein the compound is selected from the following group consisting of:

| 37 | 38 |
|---|---|
| 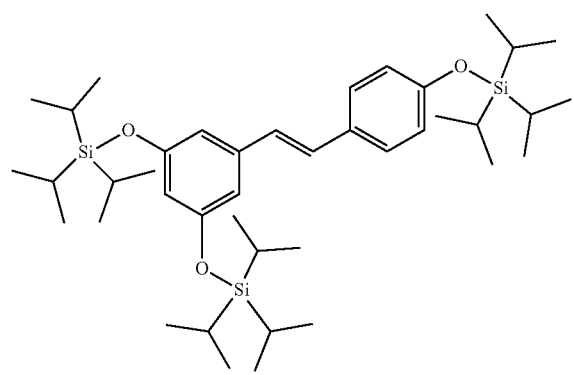 | 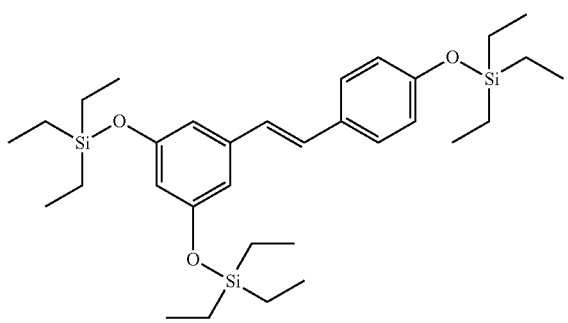 |
| 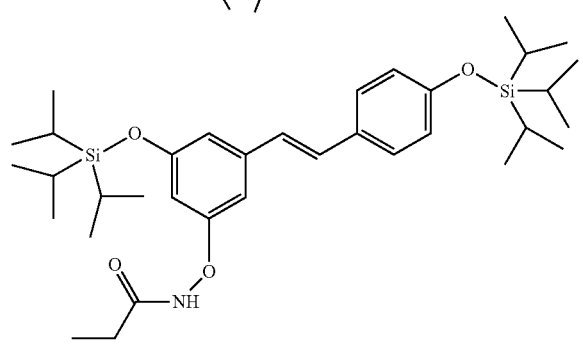 | 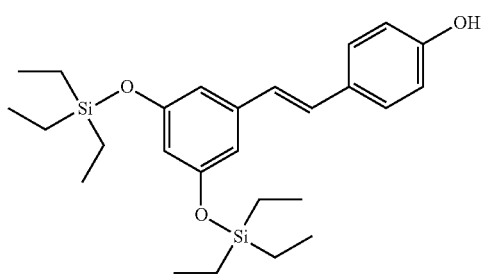 |
| 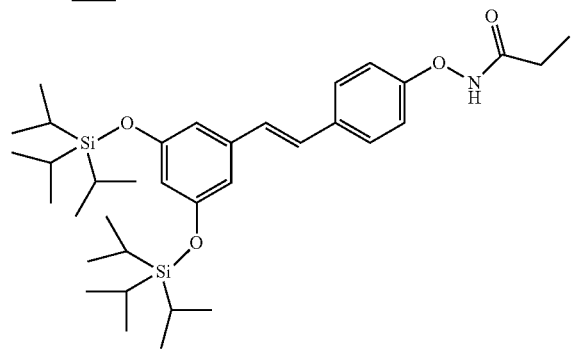 | 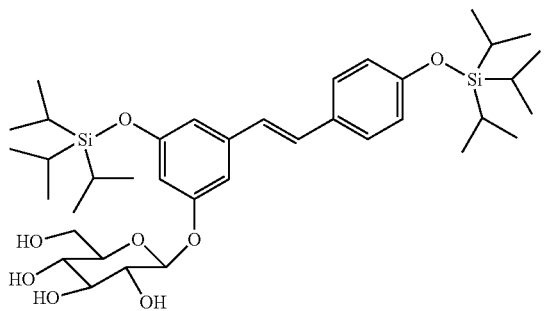 |
| 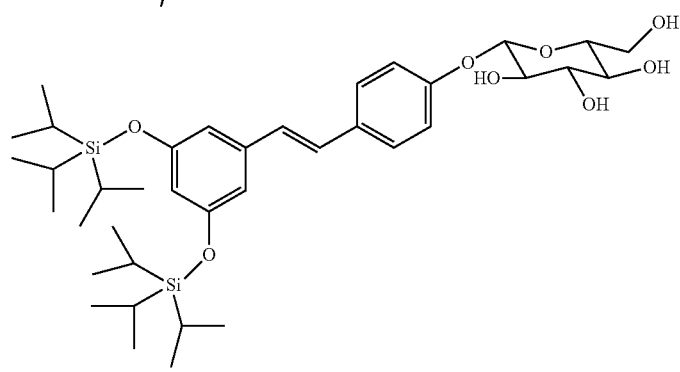 | |
| 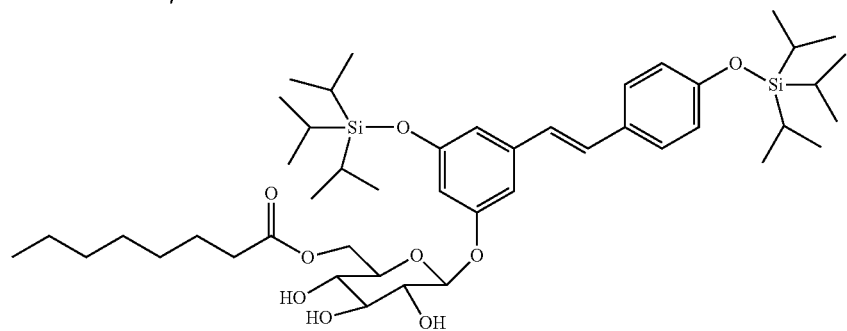 | |

-continued
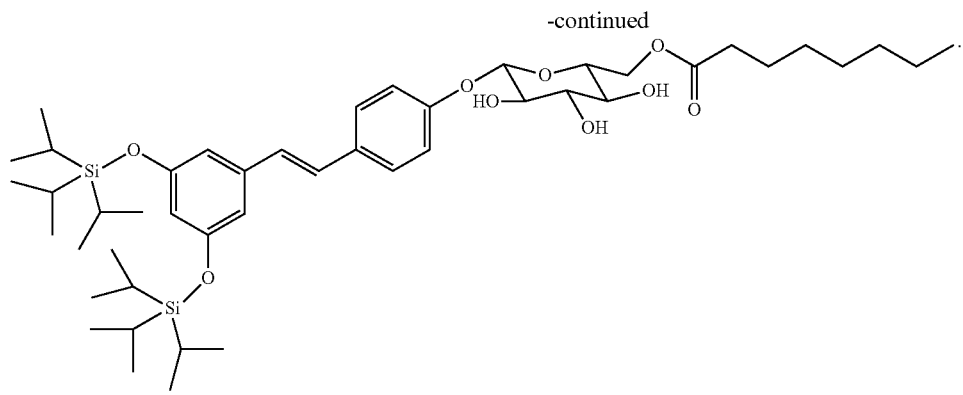
4. A pharmaceutical composition comprising the compound according to claim 1.
* * * * *

UNITED STATES PATENT AND TRADEMARK OFFICE
CERTIFICATE OF CORRECTION

PATENT NO. : 11,365,208 B2
APPLICATION NO. : 16/465536
DATED : June 21, 2022
INVENTOR(S) : Juan Carlos Morales Sánchez It is certified that error appears in the above-identified patent and that said Letters Patent is hereby corrected as shown below:

On the Title Page

Column 2 (Item (56) Other Publications), Line 32, delete "γ" and insert -- β --.

Column 2 (Item (56) Other Publications), Line 32, delete "glucopyranosideusing" and insert -- glucopyranoside using --.

Column 2 (Item (56) Other Publications), Line 33, delete "polyphenolglycoside" and insert -- polyphenol glycoside --.

Page 2, Column 1 (Item (56) Other Publications), Line 24, delete "γ" and insert -- β --.

In the Specification

Column 9, Line 45, delete "SiR4,R5,R6" and insert -- SiR4R5R6 --.

Column 9, Line 50, delete "triisopropylsylyloxy" and insert -- triisopropylsilyloxy --.

Column 21, Line 31, delete "b=7.34" and insert -- δ=7.34 --.

Column 23, Line 12, delete "dithiisopropylsilyl" and insert -- ditriisopropylsilyl --.

Column 23, Line 13, delete "dithiisopropylsilyl" and insert -- ditriisopropylsilyl --.

Column 25, Line 18, delete "5" and insert -- δ --.

Column 26, Line 12 (Approx.), delete "dithiisopropylsilyl" and insert -- ditriisopropylsilyl --.

Column 26, Line 14 (Approx.), delete "Lypozyme" and insert -- Lipozyme --.

Signed and Sealed this
Eighteenth Day of July, 2023

Katherine Kelly Vidal
*Director of the United States Patent and Trademark Office*

CERTIFICATE OF CORRECTION (continued)
U.S. Pat. No. 11,365,208 B2

Column 26, Line 38 (Approx.), delete "=1H" and insert -- δ=1H --.

Column 27, Line 3, delete "δ 7.45" and insert -- δ=7.45 --.

Column 31, Line 18, delete "PrepoTech" and insert -- PeproTech --.

Column 31, Line 39, delete "Neurodecqeneration" and insert -- Neurodegeneration --.

Column 32, Line 27, delete "dithyrylsilyl" and insert -- ditriethylsilyl --.

Column 32, Line 28, delete "-octanaoyl" and insert -- -octanoyl --.

In the Claims

Column 34, Line 34, In Claim 1, delete "C1-C6alkyl," and insert -- C1-C6 alkyl, --.